US012770009B2

(12) United States Patent
Giersch

(10) Patent No.: US 12,770,009 B2
(45) Date of Patent: Oct. 20, 2026

(54) TECHNIQUE FOR EFFICIENT RETRIEVAL OF PERSONALITY DATA

(71) Applicant: 2HFUTURA SA, Panama City (PA)

(72) Inventor: Daniel Giersch, Monaco (MC)

(73) Assignee: 2HFUTURA SA, Panama City (PA)

( * ) Notice: Subject to any disclaimer, the term of this patent is extended or adjusted under 35 U.S.C. 154(b) by 0 days.

(21) Appl. No.: 18/192,978

(22) Filed: Mar. 30, 2023

(65) Prior Publication Data

US 2023/0237338 A1 Jul. 27, 2023

Related U.S. Application Data

(63) Continuation of application No. 17/476,602, filed on Sep. 16, 2021, now Pat. No. 11,620,531, which is a (Continued)

(30) Foreign Application Priority Data

Mar. 19, 2019 (EP) .................................... 19163909

(51) Int. Cl.
*G06K 9/00* (2022.01)
*A61B 5/16* (2006.01)
(Continued)

(52) U.S. Cl.
CPC ............ *G06N 3/084* (2013.01); *A61B 5/167* (2013.01); *A61B 5/18* (2013.01); *B60W 40/09* (2013.01);
(Continued)

(58) Field of Classification Search
None
See application file for complete search history.

(56) References Cited

U.S. PATENT DOCUMENTS 6,978,245 B1 12/2005 Tsuchiya et al.
8,930,086 B2 1/2015 Khanafer
(Continued)

FOREIGN PATENT DOCUMENTS

CN 104379414 A 2/2015
CN 106537901 A 3/2017
(Continued)

OTHER PUBLICATIONS

International Search Report issued in Intl. Appln. No. PCT/EP2020/057449 mailed Jun. 5, 2020.
(Continued)

*Primary Examiner* — Wei Wen Yang
(74) *Attorney, Agent, or Firm* — ROSSI, KIMMS & McDOWELL LLP

(57) ABSTRACT

A technique for enabling efficient retrieval of a digital representation of personality data of a user (402) by a client device (406) from a server (404) is disclosed, wherein the digital representation of the personality data is processed at the client device (406) to provide a user-adapted service to the user (402). A method implementation of the technique is performed by the server (404) and comprises storing a neural network being trained to compute personality data of a user based on input obtained from the user (402), receiving, from the client device (406), a request for a digital representation of personality data for a user (402), and sending, to the client device (406), the requested digital representation of the personality data of the user (402), wherein the personality data of the user is computed using the neural network based on input obtained from the user (402).

128 Claims, 8 Drawing Sheets

Related U.S. Application Data continuation of application No. PCT/EP2020/057449, filed on Mar. 18, 2020.

(51) Int. Cl.

| | |
|---|---|
| ***A61B 5/18*** | (2006.01) |
| ***B60W 40/09*** | (2012.01) |
| ***B60W 50/06*** | (2006.01) |
| ***B62D 65/00*** | (2006.01) |
| ***G06F 16/245*** | (2019.01) |
| ***G06N 3/004*** | (2023.01) |
| ***G06N 3/04*** | (2023.01) |
| ***G06N 3/08*** | (2023.01) |
| ***G06N 3/084*** | (2023.01) |

(52) U.S. Cl.

CPC ............. *B60W 50/06* (2013.01); *B62D 65/00* (2013.01); *G06F 16/245* (2019.01); *G06N 3/004* (2013.01); *G06N 3/04* (2013.01); *G06N 3/08* (2013.01); *B60W 2540/01* (2020.02); *B60W 2540/22* (2013.01); *B60W 2540/229* (2020.02)

(56) References Cited

U.S. PATENT DOCUMENTS

| | | | |
|---|---|---|---|
| 11,537,917 | B1 | 12/2022 | Sanchez |
| 2002/0069002 | A1 | 6/2002 | Morehouse |
| 2002/0169882 | A1 | 11/2002 | Fayemi |
| 2006/0149428 | A1 | 7/2006 | Kim et al. |
| 2006/0235753 | A1 | 10/2006 | Kameyama |
| 2008/0033826 | A1 | 2/2008 | Maislos |
| 2013/0179178 | A1 | 7/2013 | Vemireddy et al. |
| 2014/0306799 | A1 | 10/2014 | Ricci |
| 2014/0309790 | A1 | 10/2014 | Ricci |
| 2014/0309839 | A1 | 10/2014 | Ricci et al. |
| 2015/0260531 | A1 | 9/2015 | Ehsani et al. |
| 2015/0370994 | A1 | 12/2015 | Madan et al. |
| 2016/0104486 | A1 | 4/2016 | Penilla |
| 2016/0170998 | A1 | 6/2016 | Frank |
| 2016/0322047 | A1 | 11/2016 | Kawashima et al. |
| 2017/0004260 | A1 | 1/2017 | Moturu |
| 2017/0102774 | A1 | 4/2017 | Naruse |
| 2017/0274908 | A1 | 9/2017 | Huai |
| 2017/0277994 | A1 | 9/2017 | Sharifi et al. |
| 2018/0061415 | A1 | 3/2018 | Penilla et al. |
| 2018/0357473 | A1 | 12/2018 | Soma et al. |
| 2019/0005417 | A1 | 1/2019 | Olsher |
| 2019/0073547 | A1 | 3/2019 | El Kaliouby et al. |
| 2019/0258850 | A1 | 8/2019 | Rihn et al. |
| 2019/0276037 | A1* | 9/2019 | Ito ............................ G08G 1/16 |
| 2019/0287392 | A1 | 9/2019 | Bielby |
| 2019/0291719 | A1 | 9/2019 | Tiziani |
| 2019/0344846 | A1 | 11/2019 | Ohno |
| 2019/0384410 | A1 | 12/2019 | Saito et al. |
| 2020/0137001 | A1 | 4/2020 | Wu |
| 2020/0152197 | A1 | 5/2020 | Penilla et al. |
| 2020/0164882 | A1 | 5/2020 | Beiderbeck |
| 2020/0330018 | A1 | 10/2020 | Lee et al. |
| 2021/0074406 | A1 | 3/2021 | Eich et al. |
| 2022/0000406 | A1 | 1/2022 | Giersch |
| 2022/0001880 | A1 | 1/2022 | Giersch |
| 2024/0394604 | A1 | 11/2024 | Arditi |

FOREIGN PATENT DOCUMENTS

| | | | |
|---|---|---|---|
| CN | 108364131 | A | 8/2018 |
| CN | 108471991 | A | 8/2018 |
| CN | 108475214 | A | 8/2018 |
| CN | 108596722 | A | 9/2018 |
| CN | 109844741 | A | 6/2019 |
| DE | 102017208159 | A1 | 11/2018 |
| EP | 1383430 | A1 | 1/2004 |
| EP | 1383430 | B1 | 12/2010 |
| EP | 3712896 | A1 | 9/2020 |
| JP | H04250171 | A | 9/1992 |
| JP | H11259446 | A | 9/1999 |
| JP | 2000222688 | A | 8/2000 |
| JP | 2001092882 | A | 4/2001 |
| JP | 2004149035 | A | 5/2004 |
| JP | 2004302826 | A | 10/2004 |
| JP | 2005195476 | A | 7/2005 |
| JP | 2007269268 | A | 10/2007 |
| JP | 2010146174 | A | 7/2010 |
| JP | 2015133050 | A | 7/2015 |
| JP | 2015191310 | A | 11/2015 |
| JP | 2016128782 | A | 7/2016 |
| JP | 2016162459 | A | 9/2016 |
| JP | 2017033320 | A | 2/2017 |
| JP | 2017078650 | A | 4/2017 |
| JP | 2019219835 | A | 12/2019 |
| WO | 2013103810 | A1 | 7/2013 |
| WO | 2015125329 | A1 | 8/2015 |
| WO | 2017022205 | A1 | 2/2017 |
| WO | 2019000326 | A1 | 1/2019 |
| WO | 2020006154 | A2 | 1/2020 |
| WO | 2020056331 | A1 | 3/2020 |
| WO | 2020187984 | A1 | 9/2020 |

OTHER PUBLICATIONS

Written Opinion issued in Intl. Appln. No. PCT/EP2020/057449 mailed Jun. 5, 2020.

International Preliminary Report on Patentability issued in Intl. Appln. No. PCT/EP2020/057449 mailed Mar. 15, 2021.

ILMINI. "Computational Personality Traits Assessment: A Review." 2017 IEEE International Conference on Industrial and Information Systems (ICIIS). Dec. 15, 2017: 1-6.

Extended European Search Report issued in European Appln. No. 19163909.5 mailed Aug. 26, 2019.

Partial International Search Report issued in Intl. Appln. No. PCT/EP2020/076436 mailed Nov. 20, 2020.

International Search Report issued in Intl. Appln. No. PCT/EP2020/076436 mailed Apr. 6, 2021.

Written Opinion issued in Intl. Appln. No. PCT/EP2020/076436 mailed Apr. 6, 2021.

GALATSIS. "Vehicle Cabin Air Quality Monitor for Fatigue and Suicide Prevention." SAE Technical Paper Series. Mar. 6, 2000: 1-5. XP055778614.

Yurtsever. "A Survey of Autonomous Driving: Common Practices and Emerging Technologies." arXiv:1906.05113v1 [cs.RO] Jun. 12, 2019.

International Search Report issued in Intl. Appln. No. PCT/EP2021/057022 mailed Jun. 16, 2021.

Written Opinion issued in Intl. Appln. No. PCT/EP2021/057022 mailed Jun. 16, 2021.

Fraunhofer IAIS. CeBIT 2017: Big Data and Machine Learning for Smart Products and Business Models. Press Release. Feb. 16, 2017: 1-3. English translation provided.

Fraunhofer IAIS. Annual Report. 2017-2018. English translation provided.

Berylls. Lifestyle Configurator. URL: https://www.berylls.com/lifestyle_konfigurator/ Web. Feb. 26, 2019. English translation provided.

HE. Neural Collaborative Filtering. arXiv:1708.05031v2 [cs.IR] Aug. 26, 2017.

Office Action issued in copending U.S. Appl. No. 17/476,602 mailed Dec. 20, 2021.

Amendment filed in copending U.S. Appl. No. 17/476,602 on Mar. 18, 2022.

Notice of Allowance issued in copending U.S. Appl. No. 17/476,602 mailed Apr. 6, 2022.

International Preliminary Report on Patentability issued in Intl. Appln. No. PCT/EP2020/076436 mailed Jun. 7, 2022.

Notice of Allowance issued in copending U.S. Appl. No. 17/476,602 mailed Aug. 1, 2022.

(56) References Cited

OTHER PUBLICATIONS

Extended European Search Report issued in European Appln. No. 22157359.5 mailed Jun. 1, 2022.
Extended European Search Report issued in European Appln. No. 22157353.8 mailed Jun. 1, 2022.
International Preliminary Report on Patentability issued in Intl. Appln. No. PCT/EP2021/057022 mailed Jun. 7, 2022.
Giersch. Copending U.S. Appl. No. 17/941,351, filed Sep. 9, 2022 (a copy is not included because the cited application is not yet available to the public and the Examiner has ready access to the cited application).
Giersch. Copending U.S. Appl. No. 17/941,309, filed Sep. 9, 2022 (a copy is not included because the cited application is not yet available to the public and the Examiner has ready access to the cited application).
Office Action issued in European Patent Appln. No. 20713243.2 mailed Sep. 28, 2022.
Office Action issued in Japanese Appln. No. 2022-504332 mailed Nov. 22, 2022. English translation provided.
Office Action issued in Japanese Appln. No. 2021-193377 mailed Nov. 22, 2022. English translation provided.
Office Action issued in Japanese Appln. No. 2021-193344 mailed Nov. 22, 2022. English translation provided.
Notice of Allowance issued in copending U.S. Appl. No. 17/476,602 mailed Jan. 12, 2023.
Notice of Allowance issued in Japanese Appln. No. 2021-193344 mailed Aug. 1, 2023. English translation provided.
Office Action issued in Chinese Appln. No. 202080022108.4 mailed Aug. 21, 2023. English translation provided.
Notice of Allowance issued in Japanese Appln. No. 2022-504332 mailed Aug. 1, 2023. English translation provided.
Notice of Allowance issued in Japanese Appln. No. 2021-193377 mailed Aug. 1, 2023. English translation provided.
Office Action issued in U.S. Appl. No. 17/476,614 mailed Jan. 23, 2024.
Office Action issued in U.S. Appl. No. 17/476,635 mailed Feb. 8, 2024.
Notification to Grant Patent Right for Invention issued in Chinese Appln. No. 202080022108.4 mailed Mar. 15, 2024. English translation provided.
John et al. "The Big-Five Trait Taxonomy: History, Measurement, and Theoretical Perspectives". Handbook of personality: Theory and research (2nd ed.). Mar. 5, 1999, pp. 1-71.
Office Action issued in copending U.S. Appl. No. 17/941,351 mailed Sep. 18, 2024.
Office Action issued in copending U.S. Appl. No. 17/941,309 mailed Sep. 23, 2024.
Office Action issued in copending U.S. Appl. No. 17/476,614 mailed Sep. 25, 2024.
Office Action issued in copending U.S. Appl. No. 17/476,635 mailed Oct. 17, 2024.
Office Action issued in Japanese Appln. No. 2022-556001 mailed May 21, 2024. English translation provided.
Office Action issued in Japanese Appln. No. 2022-556171 mailed Jun. 11, 2024. English translation provided.
Office Action issued in Chinese Appln. No. 202111595105.2 mailed Aug. 5, 2024. English translation provided.
Office Action issued in Japanese Appln. No. 2023-169513 mailed Aug. 6, 2024. English translation provided.
Office Action issued in Chinese Appln. No. 202080099928.3, mailed Nov. 5, 2024. English translation provided.
Office Action issued in Chinese Appln. No. 202210076801.0, mailed Feb. 27, 2025. English translation provided.
Decision to Grant issued in Japanese Appln. No. 2022-556171, mailed Jan. 21, 2025.
Office Action issued in Japanese Appln. No. 2022-556001, mailed Feb. 18, 2025.
Decision to Grant issued in Japanese Appln. No. 2023-169513, mailed Mar. 25, 2025.
Office Action issued in U.S. Appl. No. 17/476,614, mailed Apr. 30, 2025.
Office Action issued in U.S. Appl. No. 17/941,351, mailed May 14, 2025.
Office Action issued in U.S. Appl. No. 17/476,635, mailed May 16, 2025.
Office Action issued in U.S. Appl. No. 17/941,309, mailed Jul. 29, 2025.
Office Action issued in Chinese Appln. No. 202111595105.2, mailed Mar. 31, 2025.
Office Action issued in Chinese Appln. No. 202080099928.3, mailed Jul. 2, 2025.
Communication Pursuant to Article 94(3) EPC issued in European Appln. No. 20772088.9 mailed Jul. 16, 2025.
Communication Pursuant to Article 94(3) EPC issued in European Appln. No. 21712175.5 mailed Jul. 16, 2025.
Communication Under Rule 71(3) EPC issued in European Appln. No. 20713243.2 mailed Jul. 22, 2025.
Communication Under Rule 71(3) EPC issued in European Appln. No. 22157353.8 mailed Jul. 22, 2025.
Communication Under Rule 71(3) EPC issued in European Appln. No. 22157359.5 mailed Jul. 22, 2025.
Office Action issued in Chinese Appln. No. 202111595105.2 mailed Aug. 28, 2025.
Brenner "Artificial Neural Networks: What Every Marketer Should Know", Marketing Insider Group, Jan. 23, 2018, pp. 1-12. https://marketinginsidergroup.com/content-marketing/artificial-neural-networks-every-marketer-know/.
"Input nodes" IBM App Connect Enterprise Software 12.0.12.19 Operating Systems: AIX, Linux, Windows. Updated 2025, pp. 1-4. https://www.ibm.com/docs/en/app-connect/12.0.x?topic=use-input-nodes.
Office Action issued in U.S. Appl. No. 17/941,351 mailed Dec. 9, 2025.
Office Action issued in U.S. Appl. No. 17/476,635 mailed Feb. 2, 2026.
Notice of Allowance issued in U.S. Appl. No. 17/476,614 mailed Feb. 4, 2026.
Rejection Decision issued in Chinese Appln. No. 202080099928.3 mailed Nov. 18, 2025.
Final Office Action issued in Japanese Appln. No. 2022-556001 mailed Dec. 2, 2025.
Notification to Grant Patent Right for Invention issued in Chinese Appln. No. 202210076801.0 mailed Jan. 7, 2026.
Decision to Grant a Patent issued in Japanese Appln. No. 2022-556001 mailed Jan. 27, 2026.
Notification to Grant Patent Right for Invention issued in Chinese Appln. No. 202111595105.2 mailed Jan. 29, 2026.
Communication under Rule 71(3) EPC issued in European Appln. No. 20713243.2 mailed Mar. 9, 2026.
Communication under Rule 71(3) EPC issued in European Appln. No. 22157353.8 mailed Mar. 10, 2026.
Communication under Rule 71(3) EPC issued in European Appln. No. 22157359.5 mailed Mar. 10, 2026.
"Apple iPhone iOS 11 User Guide" (iPhone 8 / iPhone X manual), pp. 86-90, available at "https://archive.org/details/apple-iphone-ios-11-iphone-8-iphone-x-manual/page/n85/mode/2up" published at this archive on Jan. 18, 2018.
Screen shots of the video "Siri Demo by Scott Forstall at Apple Special Event Oct. 4, 2011, available at https://www.youtube.com/watch?v=SpGJNPShzRc".
Use Siri in your car. available at "https://support.apple.com/guide/iphone/use-siri-in-your-car-iphadacf963f/12.0/ios/12.0" retrieved on Apr. 20, 2026.
Office Action issued in Japanese Appln. No. 2025-047043 mailed Jun. 16, 2026.
Office Action issued in U.S. Appl. No. 17/941,351 mailed Jul. 7, 2026.
Communication under Rule 71(3) EPC issued in European Appln. No. 22157353.8 mailed Jul. 28, 2026.
Communication under Rule 71(3) EPC issued in European Appln. No. 20713243.2 mailed Aug. 10, 2026.

(56) References Cited

OTHER PUBLICATIONS

Office Action issued in Chinese Appln. No. 2021800295129 mailed Aug. 29, 2026.
Notice of Panel Decision issued in U.S. Appl. No. 17/476,635 mailed Aug. 21, 2026.

* cited by examiner

TECHNIQUE FOR EFFICIENT RETRIEVAL OF PERSONALITY DATA

CROSS-REFERENCE TO RELATED APPLICATIONS

This application is a continuation of U.S. patent application Ser. No. 17/476,602, filed Sep. 16, 2021, now U.S. Pat. No. 11,620,531 issued Apr. 4, 2023, which is a bypass continuation of prior Patent Cooperation Treaty ("PCT") International Application No. PCT/EP2020/057449, filed Mar. 18, 2020, which claims priority benefit of European Patent Application No. 19163909.5, filed Mar. 19, 2019. The entire disclosure of each of the applications cited in this section is hereby incorporated herein by reference.

TECHNICAL FIELD

The present disclosure generally relates to the field of data retrieval. In particular, a technique for enabling efficient retrieval of a digital representation of personality data of a user by a client device from a server is presented. The technique may be embodied in methods, computer programs, apparatuses and systems.

BACKGROUND

Personality tests have been used for decades to assess people's personality characteristics and are typically performed based on personality survey data obtained from a person to be tested, wherein the survey data is evaluated by a professional, such as a psychologist, to conclude on the person's personality. The so called "OCEAN" model is a widely accepted taxonomy for personality traits, also known as the "Big Five" personality traits, and includes openness, conscientiousness, extraversion, agreeableness and neuroticism as personality dimensions. Widely known personality tests using the OCEAN model include tests based on the so called International Personality Item Pool (IPIP), the HEXACO-60 inventory and the Big-Five-Inventory-10 (BFI-10), for example, which comprise sets of questions for testing a person on each of the five personality dimensions. As conventional personality tests generally require a review by a human professional, such as a psychologist, to obtain a qualified assessment of a person's personality traits, however, it is difficult to integrate carrying out personality tests and their results into processes performed on technical systems, although such integration could be beneficial because it would allow adapting processes to better fit a user's personality and, therefore, to improve user experience, such as by providing user-adapted services to the user, for example.

SUMMARY

Accordingly, there is a need for a technical implementation which makes the integration of personality tests and their results into processes performed on technical systems practically feasible.

According to a first aspect, a method for enabling efficient retrieval of a digital representation of personality data of a user by a client device from a server is provided, wherein the digital representation of the personality data is processed at the client device to provide a user-adapted service to the user. The method is performed by the server and comprises storing a neural network being trained to compute personality data of a user based on input obtained from the user, receiving, from the client device, a request for a digital representation of personality data for a user, and sending, to the client device, the requested digital representation of the personality data of the user, wherein the personality data of the user is computed using the neural network based on input obtained from the user.

By storing a trained neural network on the server and applying it for computing personality data of a user, retrieval of a digital representation of the personality data of the user may be made automatable (as conventional human reviews may no longer be needed) and, as such, an integration of the retrieval and use of users' personality data into (e.g., automated) processes performed on technical systems may become feasible. In particular, the neural network may be seen as an efficient functional data structure which enables computing the requested personality data in a single computational run, i.e., by inputting the input obtained from the user at the input nodes of the neural network and reading off the resulting output values representative of the personality data from the output nodes of the neural network. As such, the neural network may enable an efficient provision of personality data in the form of a digital representation to the client device, where it may be used to provide a service adapted to the particular personality of the user, to thereby improve user experience on the side of the client device. Due to the efficient provision of data, the integration of retrieval and use of personality data may especially become practical as the digital representation of the personality data may be provided to the client device without significant delay and may be processed at the client device instantly. A technical implementation may therefore be achieved which generally makes integrating the retrieval and use of personality data into processes performed on technical systems practically feasible.

The personality data of the user may be indicative of psychological characteristics and/or preferences of the user and, as such, the personality data may generally include psychological data as well as medical data (e.g., data indicating a tendency to curiosity, anxiety, depression, etc.), including classical personality data which may be based on the personality dimensions of openness, conscientiousness, extraversion, agreeableness and neuroticism (known as the Big Five, as described above), for example. The digital representation of the personality data of the user may comprise a digital representation of the mentioned characteristics, such as a digital representation of at least one of the personality dimensions of openness, conscientiousness, extraversion, agreeableness and neuroticism, as computed by the neural network for the user, for example.

The client device may be configured to process the digital representation of the personality data for the purpose of enabling the provision of a user-adapted service to the user. In one variant, the client device may itself be configurable based on the digital representation of the personality data. An exemplary device which may be configurable by the digital representation of the personality data may be a vehicle, for example. The vehicle may in this case be the client device. The vehicle may process the received digital representation of the personality data of the user (e.g., a driver of the vehicle) and configure itself (e.g., including subcomponents thereof) so as to adapt the vehicle's driving configuration to the personality of the driver and to thereby provide a driving service that is specifically adapted to the personality of the user. If the personality data indicates that the driver tends to be risk-averse or anxious, for example, the vehicle's driving configuration may be configured to be more safety-oriented, whereas for drivers that tend to have a more risk-seeking personality, the vehicle's driving configuration may be configured to be more sporty. To this end, among other settings, the gas and brake reaction behavior of the vehicle may be adapted accordingly. Subcomponents of the vehicle providing vehicle-related services may be configured based on the personality data as well, such as a sound system of the vehicle including its sound and volume settings to better comply with the user's personality, for example.

In another variant, the client device may configure at least one other device based on the digital representation of the personality data, e.g., when it is the at least one other device that provides the service to the user. In such a variant, the client device may be a mobile terminal (e.g., a smartphone), for example, which may interface (e.g., using Bluetooth) with the vehicle (i.e., in this case, the vehicle corresponds to the at least one other device) and, upon receipt of the digital representation of the personality data from the server, the mobile terminal may configure the vehicle via the interface. It may thus be said that the digital representation of the personality data of the user may be processed at the client device to configure at least one device providing a service to the user. Configuring the at least one device may comprise configuring at least one setting of the at least one device and/or configuring at least one setting of a service provided by the at least one device. It will be understood that the vehicle is merely an example of a device which may be configurable based on personality data and that the client device and/or the at least one other device may correspond to other types of devices as well.

In one implementation, the method performed by the server may further comprise receiving feedback characterizing the user, updating the neural network based on the feedback, and sending, to the client device, a digital representation of updated personality data of the user, wherein the updated personality data of the user may be computed using the updated neural network. The digital representation of the updated personality data of the user may be processed at the client device to refine a configuration of the at least one device providing the service to the user (e.g., one of the configurations of the vehicle mentioned above). The feedback may be gathered at the client device and/or at the at least one device providing the service to the user and may be indicative of the personality of the user. The feedback may include behavioral data reflecting behavior of the user monitored at the at least one device when using the service provided by the at least one device, for example, wherein, in one variant, the behavioral data may be monitored using (e.g., sensor based) measurements performed by the at least one device providing the service to the user. In the vehicle example, the behavior of the user being monitored may be the driving behavior of the user and the driving behavior may be measured by sensors at the vehicle, for example. For measuring the driving behavior, the sensors may sense the user's brake reaction and intensity, for example, and, since such measurements may be indicative of a user's personality (e.g., aggressiveness in driving), this information may be sent as feedback to the server in order to update the neural network and thereby refine the neural network's capability to compute personality data of users.

Updating the neural network may include training the neural network based on the feedback received from the client device, wherein, if the feedback represents a new input value which has not yet been input to the neural network, a new input node may be added to the neural network and the new input value may be assigned to the new input node when training the neural network. This makes the power of the neural network as an efficient functional data structure employed in the technical implementation presented herein especially apparent: the neural network represents an efficiently updatable data structure which may be updated based on arbitrary feedback on the user's personality received from the client device to refine its capability to compute personality data. The information conveyed by the feedback can be directly integrated into the neural network and may, once trained, immediately be reflected in subsequent requests sent to the server requesting digital representations of personality data. Conventional personality assessment techniques are rather fixed and may not support such updatability at all.

The digital representation of the personality of the user sent from the server to the client device may correspond to a digital representation of the personality of the user which was previously computed by the server upon a previous request for computing the personality of the user (e.g., upon performing a personality test by answering a set of questions by the user). The personality data of the user may thus be computed prior to receiving the request from the client device, wherein the request may include an access code previously provided by the server to the user upon computing the personality data of the user, wherein the access code allows the user to access the digital representation of the personality data of the user from different client devices. Such implementation may save computational resources at the server since the digital representation of the personality of the user may not have to be computed anew each time the digital representation of the personality data for that particular user is requested from a client device, but may be returned on the basis of the pre-computed personality data. The user, in turn, may use the access code to access the digital representation of personality data from a plurality of different client devices, such as from different vehicles the user may drive, e.g., a car and a motorcycle, or other types of devices.

The input obtained from the user may correspond to digital scores reflecting answers to questions regarding at least one of personality, goals and motivations of the user (as obtained in a question answer scheme in the manner of a personality test, for example), wherein each digital score may be used as input to a separate input node of the neural network when computing the personality data of the user using the neural network. The digital scores may correspond to a five level Likert scale having values from 1 to 5, for example. The neural network may correspond to a deep neural network having at least two hidden layers between the input layer comprising the input nodes and the output layer comprising the output nodes of the neural network. The questions relating to personality may correspond to questions of the conventional IPIP, HEXACO-60 and/or BFI-10 pools, for example, but it will be understood that other questions regarding the personality of the user may be used as well, including questions on psychological characteristics and/or preferences of the user. Questions specifically relating to goals and motivations of the user may define additional dimensions (e.g., in addition to the Big Five) that may increase the accuracy of the computed personality data over the conventional IPIP, HEXACO-60 and BFI-10 techniques. The network may be trained based on data collected in a basic survey conducted with a plurality of test persons (e.g., 1000 or more), wherein the basic survey may be carried out using the questions mentioned above.

In order to reduce the computational complexity when computing the personality data of the user, the neural network may be designed to have a specific network structure. In view of the context of the above questions, the structure of the neural network may generally be designed such that the number of input nodes is reduced as compared to the number of input nodes available when all of the above questions were used. The questions may thus correspond to questions selected from a set of questions representative of an optimally achievable result of computing personality data of a user (i.e., if all questions in the set of questions were answered by the user), wherein the selected questions may correspond to questions of the set of questions which are determined to be most influential with respect to the optimally achievable result. As each answer to a question may be input to a separate input node of the neural network, as described above, selecting a subset of the set of questions may reduce the number of input nodes when computing the personality data to thereby reduce the computational complexity. Due to the fact that questions which are most influential with respect to the achievable result are selected, the accuracy of the result output by the neural network may approximately be maintained.

In fact, tests have shown that the number of questions may be reduced drastically without significantly sacrificing result accuracy. Taking, as the set of questions being representative of an optimally achievable result of computing personality data, a set of questions which comprises the standard IPIP, HEXACO-60 and BFI-10 questions (summing up to a total number of 370 questions), optionally supplemented by further questions regarding goals and motivations of the user (resulting in a number of more than 370 questions in total), tests have shown that, when only the 30 most influential questions are used, approximately 90% of the accuracy of the optimally achievable result can be achieved. As such, the number of the selected questions may be less than 10% (preferably less than 5%) of the number of questions included in the set of questions being representative of the optimally achievable result. As, in this case, the number of input nodes of the neural network may be reduced extensively, computational resources may be saved significantly and personality data may be computed more efficiently.

In order to determine the questions of the set of questions which are most influential with respect to the optimally achievable result, in one variant, the questions may be selected from the set of questions based on correlating results achievable by each single question of the set of questions with the optimally achievable result and selecting questions from the set of questions which have the highest correlation with the optimally achievable result. A fixed subset of the set of questions being representative of the optimally achievable result may thus be determined, which may then be used to train the neural network with a reduced number of input nodes, as described above.

As said, the optimally achievable result may correspond to a result which is achieved if all questions in the set of questions were answered by the user, such as the set of questions comprising the standard IPIP, HEXACO-60 and BFI-10 questions, optionally supplemented by further questions regarding goals and motivations of the user, as described above. While, in one variant, the standard IPIP scores (as obtained by answering all questions in the standard IPIP test), the standard HEXACO-60 scores (as obtained by answering all questions in the standard HEXACO-60 test) and the standard BFI-10 scores (as obtained by answering all questions in the standard BFI-10 test) may be taken individually as reference for the optimally achievable result, in another variant, an improvement may be achieved by calculating a combined score of these individual scores as reference for the optimally achievable result, wherein the combined score may be calculated as a (e.g., weighted) average of the individual scores, for example. The combined score may also be denoted as a "superscore" representative of the "truth" derivable from the individual scores, generally improving the meaningfulness of the determined score and representing an improved reference for the optimally achievable result.

In another variant, the questions may be selected iteratively from the set of questions, wherein, in each iteration, a next question may be selected depending on an answer of the user to a previous question, and wherein, in each iteration, the next question may be selected as a question of the set of questions which is determined to be most influential on an achievable result for computing personality data of the user. This may be seen as an adaptive selection of the questions, wherein questions are determined user specifically in a stepwise manner taking into account answers to previous questions of the user. In one particular variant, the neural network may comprise a plurality of output nodes representative of a probability curve of a result of the personality data of the user, wherein determining the most influential question of the set of questions as the next question of the respective iteration may include determining, for each input node of the neural network, a degree according to which a change in the digital score which is input to the respective input node of the neural network changes the probability curve. The question associated with an input node for which the degree of change in the probability curve is determined to be highest may be selected as the most influential question for the respective iteration.

To further reduce computational complexity, the above iterative and adaptive selection may be performed under at least one constraint, such as at least one of a maximum number of questions to be selected, a minimum result accuracy to be achieved (the result accuracy may increase with each answered question per iteration and, when the desired minimal result accuracy is reached, the computation may be stopped), and a maximum available time (the test may be stopped upon lapse of the maximum available time, or each question may be associated with an estimated time to be answered by the user and the number of questions to be selected may be determined based on the estimated times). These constraints may be configurable for each computation of personality data separately.

According to a second aspect, a method for enabling efficient retrieval of a digital representation of personality data of a user by a client device from a server is provided. The method is performed by the client device and comprises sending, to the server, a request for a digital representation of personality data for a user, receiving, from the server, the requested digital representation of the personality data of the user, the personality data of the user being computed, based on input obtained from the user, using a neural network trained to compute personality data for a user based on input obtained from the user, and processing the digital representation of the personality data to provide a user-adapted service to the user.

The method according to the second aspect defines a method from the perspective of a client device which may be complementary to the method performed by the server according to the first aspect. The server and the client device of the second aspect may correspond to the server and the client device described above in relation to the first aspect. As such, those aspects described with regard to the method of the first aspect which are applicable to the method of the second aspect may be comprised by the method of the second aspect as well, and vice versa. Unnecessary repetitions are thus omitted in the following.

As in the method of the first aspect, the digital representation of the personality data of the user may be processed at the client device to configure at least one device providing a service to the user, wherein the at least one device may comprise the client device. The method performed by the client device may further comprise sending, to the server, feedback characterizing the user, and receiving, from the server, a digital representation of updated personality data of the user, wherein the updated personality data of the user may be computed using the neural network being updated based on the feedback. The digital representation of the updated personality data of the user may be processed at the client device to refine a configuration of the at least one device providing the service to the user. The feedback may include behavioral data reflecting behavior of the user monitored at the at least one device when using the service provided by the at least one device, wherein the behavioral data may be monitored using measurements performed by the at least one device providing the service to the user. The at least one device may comprise a vehicle, wherein the behavioral data may comprise data reflecting a driving behavior of the user. The personality data of the user may be computed prior to sending the request to the server, wherein the request may include an access code previously provided by the server to the user upon computing the personality data of the user, the access code allowing the user to access the digital representation of the personality data of the user from different client devices. The input obtained from the user may correspond to digital scores reflecting answers to questions regarding at least one of personality, goals and motivations of the user.

According to a third aspect, a computer program product is provided. The computer program product comprises program code portions for performing the method of at least one of the first aspect and the second aspect when the computer program product is executed on one or more computing devices (e.g., a processor or a distributed set of processors). The computer program product may be stored on a computer readable recording medium, such as a semiconductor memory, DVD, CD-ROM, and so on.

According to a fourth aspect, a server for enabling efficient retrieval of a digital representation of personality data of a user by a client device from the server is provided, wherein the digital representation of the personality data is processed at the client device to provide a user-adapted service to the user. The server comprises at least one processor and at least one memory, wherein the at least one memory contains instructions executable by the at least one processor such that the server is operable to perform any of the method steps presented herein with respect to the first aspect.

According to a fifth aspect, a client device for enabling efficient retrieval of a digital representation of personality data of a user from a server is provided. The client device comprises at least one processor and at least one memory, wherein the at least one memory contains instructions executable by the at least one processor such that the client device is operable to perform any of the method steps presented herein with respect to the second aspect.

According to a sixth aspect, there is provided a system comprising a server according to the fourth aspect and at least one client device according to the fifth aspect.

BRIEF DESCRIPTION OF THE DRAWINGS

Further details and advantages of the technique presented herein will be described with reference to exemplary implementations illustrated in the figures, in which.

DETAILED DESCRIPTION

In the following description, for purposes of explanation and not limitation, specific details are set forth in order to provide a thorough understanding of the present disclosure. It will be apparent to one skilled in the art that the present disclosure may be practiced in other implementations that depart from these specific details.

Those skilled in the art will further appreciate that the steps, services and functions explained herein below may be implemented using individual hardware circuitry, using software functioning in conjunction with a programmed microprocessor or general purpose computer, using one or more Application Specific Integrated Circuits (ASICs) and/or using one or more Digital Signal Processors (DSPs). It will also be appreciated that when the present disclosure is described in terms of a method, it may also be embodied in one or more processors and one or more memories coupled to the one or more processors, wherein the one or more memories are encoded with one or more programs that perform the steps, services and functions disclosed herein when executed by the one or more processors.

Figure 1A:
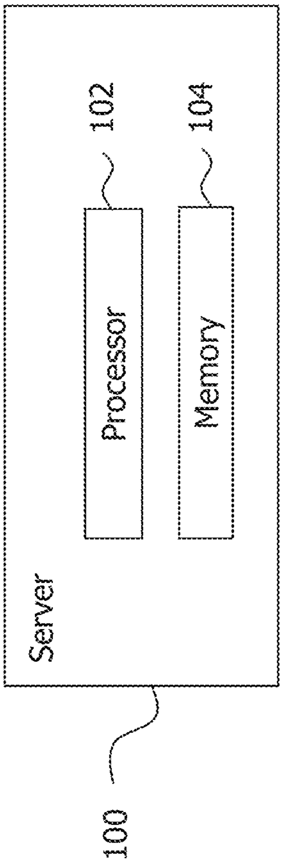
FIGS. 1*a* and 1*b* illustrate exemplary compositions of a server and a client device according to the present disclosure.

FIG. 1*a* schematically illustrates an exemplary composition of a server 100 for enabling efficient retrieval of a digital representation of personality data of a user by a client device from the server 100, wherein the digital representation of the personality data is to be processed at the client device to provide a user-adapted service to the user. The server 100 comprises at least one processor 102 and at least one memory 104, wherein the at least one memory 104 contains instructions executable by the at least one processor 102 such that the request server 100 is operable to carry out the method steps described herein with reference to the "server".

It will be understood that the server 100 may be implemented on a physical computing unit or a virtualized computing unit, such as a virtual machine, for example. It will further be appreciated that the server 100 may not necessarily be implemented on a standalone computing unit, but may be implemented as components—realized in software and/or hardware—residing on multiple distributed computing units as well, such as in a cloud computing environment, for example.

Figure 1B:
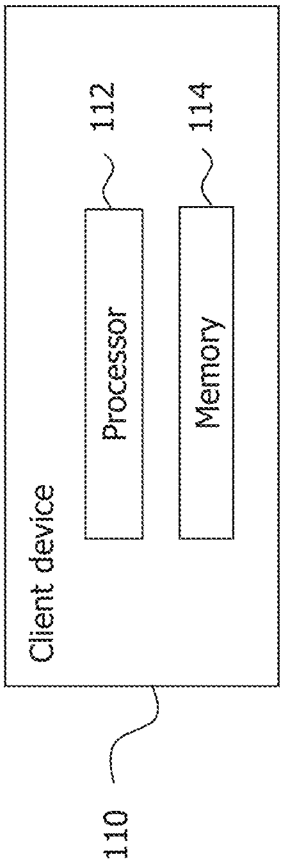

FIG. 1*b* schematically illustrates an exemplary composition of a client device 110 for enabling efficient retrieval of a digital representation of personality data of a user by the client device 110 from a server. The client device 110 comprises at least one processor 112 and at least one memory 114, wherein the at least one memory 114 contains instructions executable by the at least one processor 112 such that the request client device 110 is operable to carry out the method steps described herein with reference to the "client device".

Figure 2:
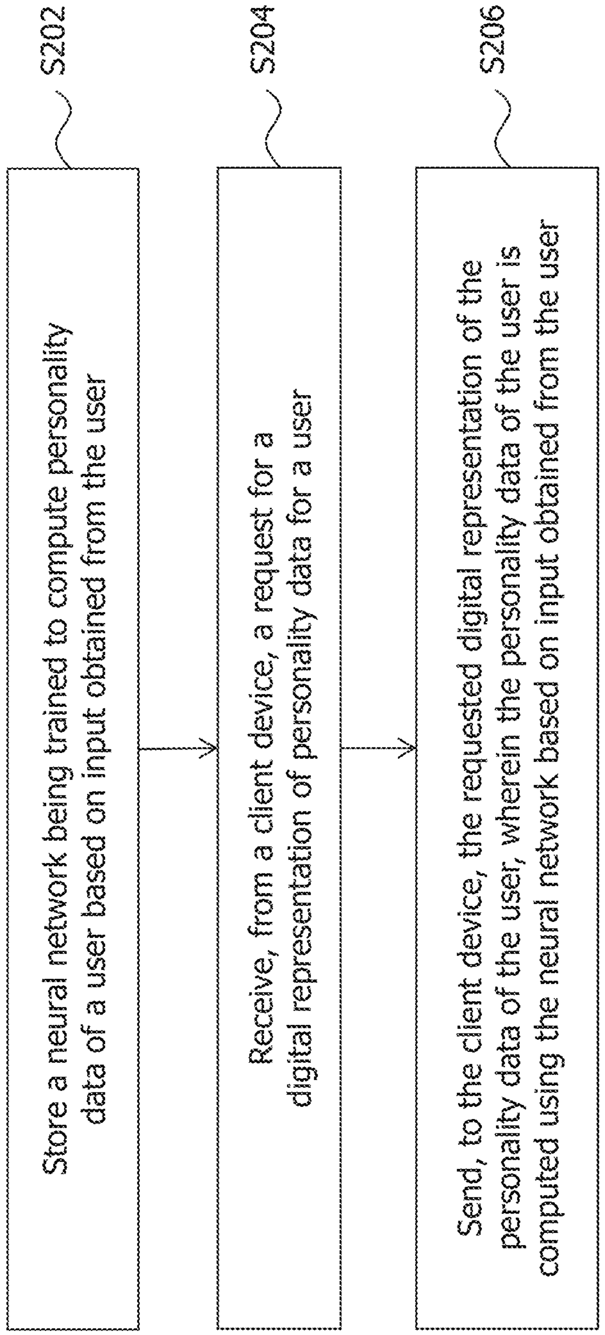
FIG. 2 illustrates a method which may be performed by the server according to the present disclosure.

FIG. 2 illustrates a method which may be performed by the server 100 according to the present disclosure. The method is dedicated to enabling efficient retrieval of a digital representation of personality data of a user by a client device (e.g., the client device 110) from the server 100. In the method, the server 100 may perform the steps described herein with reference to the "server" and, in line with the above description, in step S202, the server 100 may store a neural network being trained to compute personality data of a user based on input obtained from the user, in step S204, the server 100 may receive, from the client device, a request for a digital representation of personality data for a user and, in step S206, the server 100 may send, to the client device, the requested digital representation of the personality data of the user, wherein the personality data of the user is computed using the neural network based on input obtained from the user.

Figure 3:
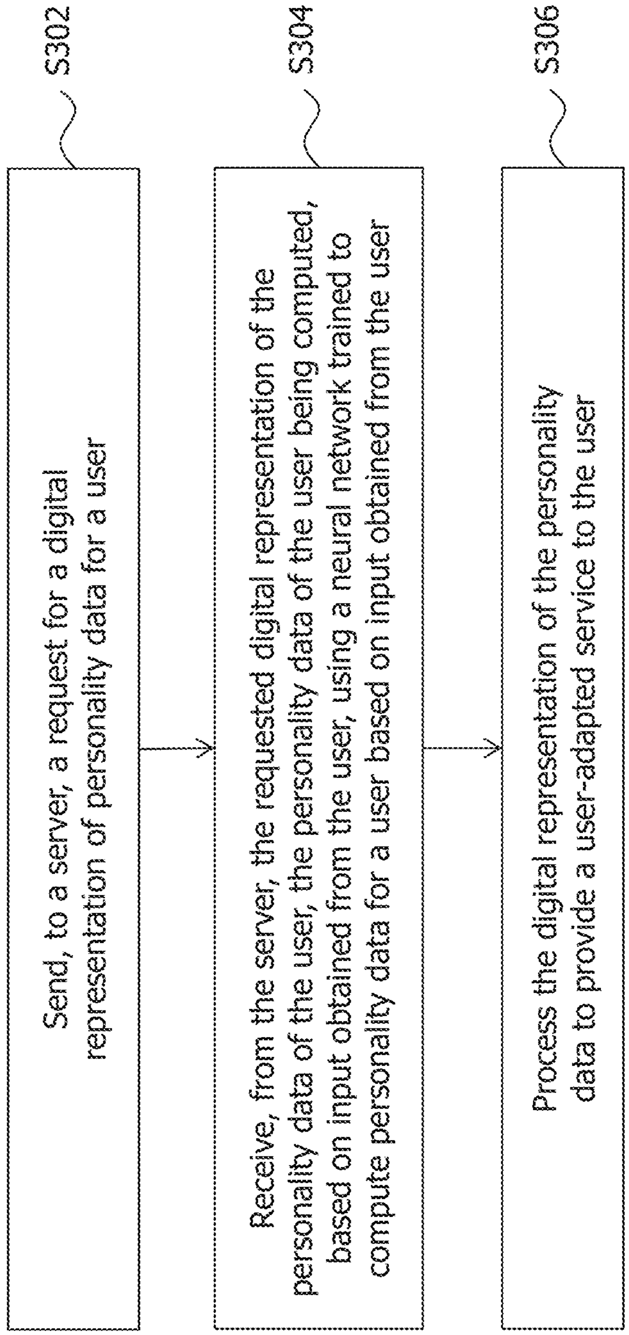
FIG. 3 illustrates a method which may be performed by the client device according to the present disclosure.

FIG. 3 illustrates a method which may be performed by the client device 110 according to the present disclosure. The method is dedicated to enabling efficient retrieval of a digital representation of personality data of a user by the client device 110 from a server (e.g., the server 100). In the method, the client device 110 may perform the steps described herein with reference to the "client device" and, in line with the above description, in step S302, the client device 110 may send, to the server, a request for a digital representation of personality data for a user, in step S304, the client device 110 may receive, from the server, the requested digital representation of the personality data of the user, the personality data of the user being computed, based on input obtained from the user, using a neural network trained to compute personality data for a user based on input obtained from the user and, in step S306, the client device 110 may process the digital representation of the personality data to provide a user adapted service to the user.

Figure 4:
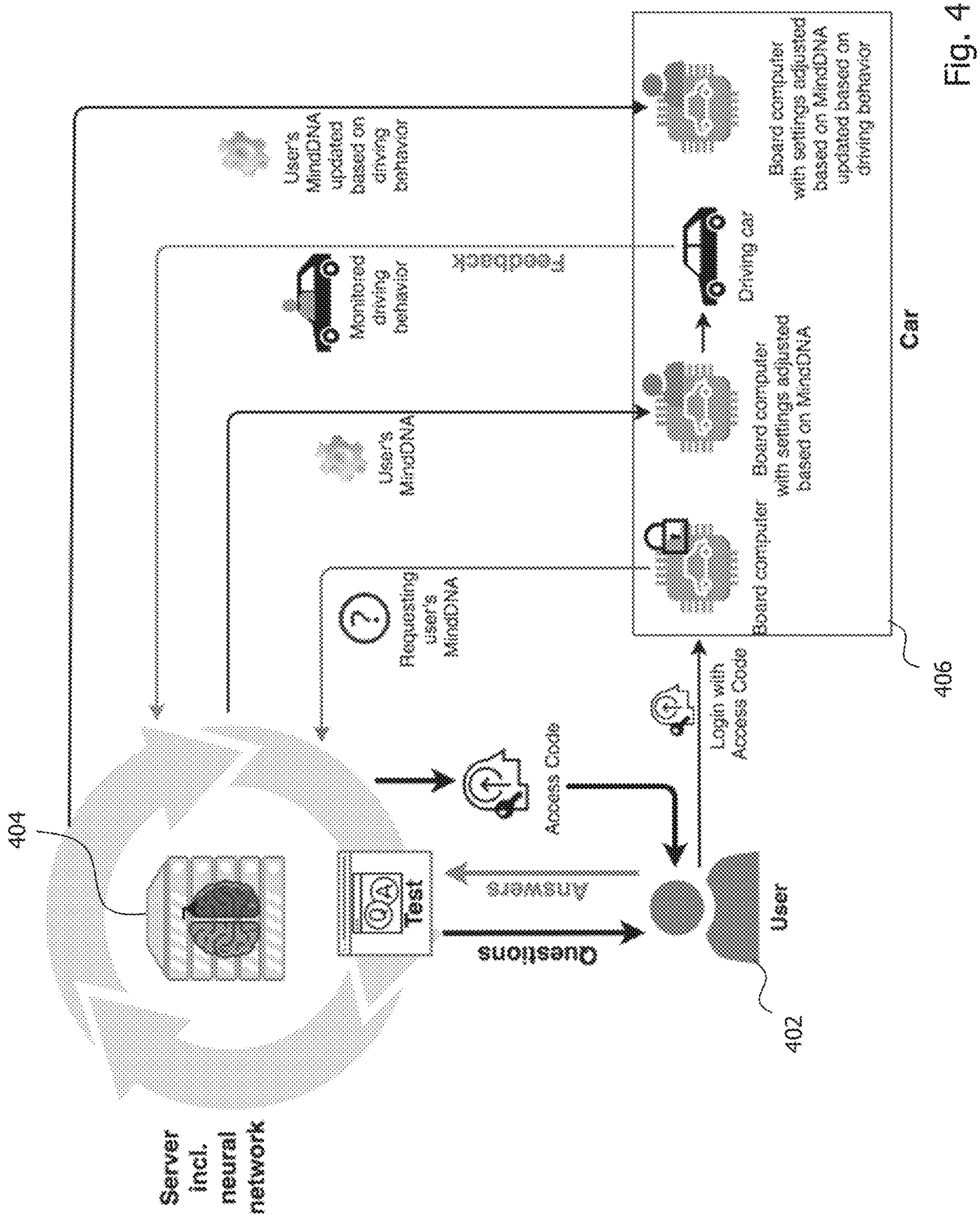
FIG. 4 illustrates an exemplary interaction between a user, the server and a client device (exemplified by a car) according to the present disclosure.

FIG. 4 illustrates an exemplary interaction between a user 402, a server 404 storing a neural network being trained to compute personality data of users based on input obtained from the users, and a client device for retrieving a digital representation of personality data of the user 402 to provide a user-adapted service to the user 402, wherein, in the shown example, the client device is a car 406 which may be driven by the user 402. As shown in the figure, the user 402 may perform an automated personality test by answering questions, e.g., using a web interface or an app on his laptop or smartphone, to thereby provide input to the neural network stored at the server 404 based on which the neural network may compute personality data for the user 402. Instead of sending a digital representation of the personality data to the user 402, in the shown example, the server 404 provides an access code to the user 402 which can be used by the user 402 to access the personality data using different client devices, including the car 406. The user 402 may register or login at the car 406 (more specifically, at its board computer) with the access code and the car 406 may then request, using the access code, the digital representation of the user's personality data from the server 404 (in the figure, the personality data of the user is denoted as the user's "MindDNA").

Upon receiving the request from the car 406, the server 404 may return the user's personality data to the car 406, which may then configure its driving configuration (and, optionally, subcomponents of the car 406) in accordance with the personality data of the user 402, e.g., adapting the gas and brake reaction behavior of the car 406, to thereby provide a driving experience that is specifically adapted to the user's personality (e.g., risk-averse, risk-seeking, etc.). When the user 402 then drives the car 406, the car 406 may monitor the user's driving behavior, e.g., using sensors measuring the user's break reaction and intensity, and the car 406 may provide this information as feedback to the server 404, where the feedback may be processed to update (by training) the neural network to refine its capability of computing the personality data of the user 402. In response, the server 404 may send correspondingly updated personality data of the user 402 to the car 406 which may then use the digital representation of the updated personality data to refine the car configuration for a better alignment with the actual personality of the user 402. In sum, a system is therefore provided which may allow integrating retrieval and use of the user's personality data into an automated process to adapt the configuration of devices or services provided thereon in accordance with the preferences of the user derived his personality data, to thereby improve user experience.

Figure 5:
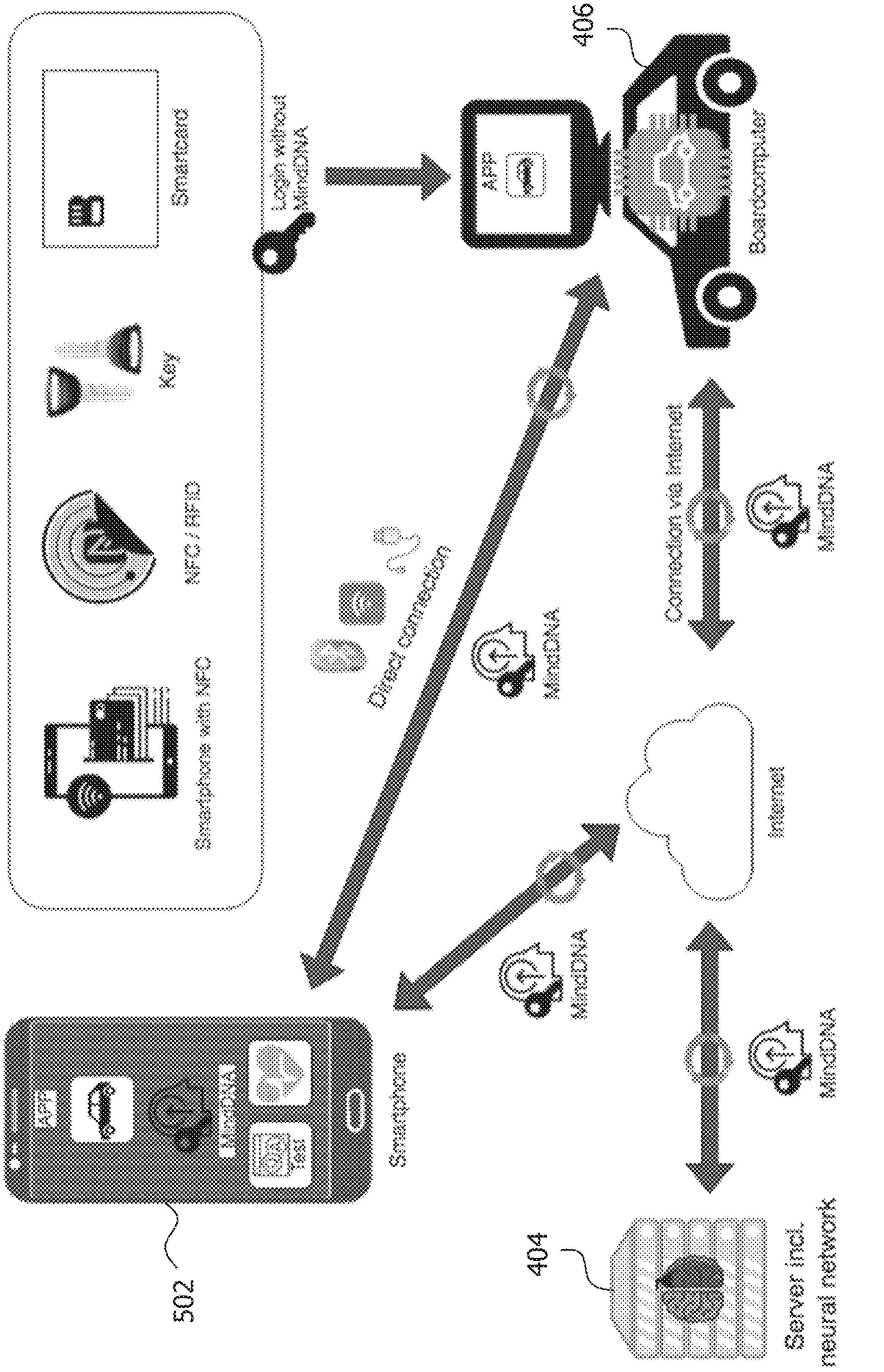
FIG. 5 illustrates different connectivity options between a mobile terminal of the user, the car and the server according to the present disclosure.

FIG. 5 illustrates different connectivity options between a mobile terminal 502 (e.g., a smartphone) of the user 402, the car 406 and the server 404 in accordance with the present disclosure. In one variant, the car 406 may communicate with the server 404 directly via the Internet and, upon authentication of the user 402 with the car 406 (e.g., using a key, smartcard, NFC/RFID, a smartphone with NFC, fingerprint, or the like), the car 406 may request the personality data of the user (in FIG. 5 again denoted as the user's "MindDNA") to improve the driving experience of the user 402. In another variant, when the user 402 carries the mobile terminal 502, the mobile terminal 502 may (e.g., using a dedicated app installed thereon) communicate with the server 404 via the Internet and request the personality data of the user 402. In this variant, the car 406 may communicate locally with the mobile terminal 502 (e.g., using Bluetooth, Wi-Fi or USB cable) and retrieve the personality data of the user from the mobile terminal 502. A direct connection between the car 406 and the mobile terminal 502 may additionally be used to exploit sensors installed at the mobile terminal 502 (e.g., gyroscope for movement and acceleration detection, GPS for movement and acceleration detection as well as detection of driving routes, or medical sensors measuring pulse, blood pressure, or the like) to supplement the feedback gathered by the car 406 itself (e.g., in relation to the user's driving behavior) to thereby provide additional feedback sensed by the mobile terminal 502 to the server 404 for updating the neural network based on the feedback, as described above.

Figure 6A:
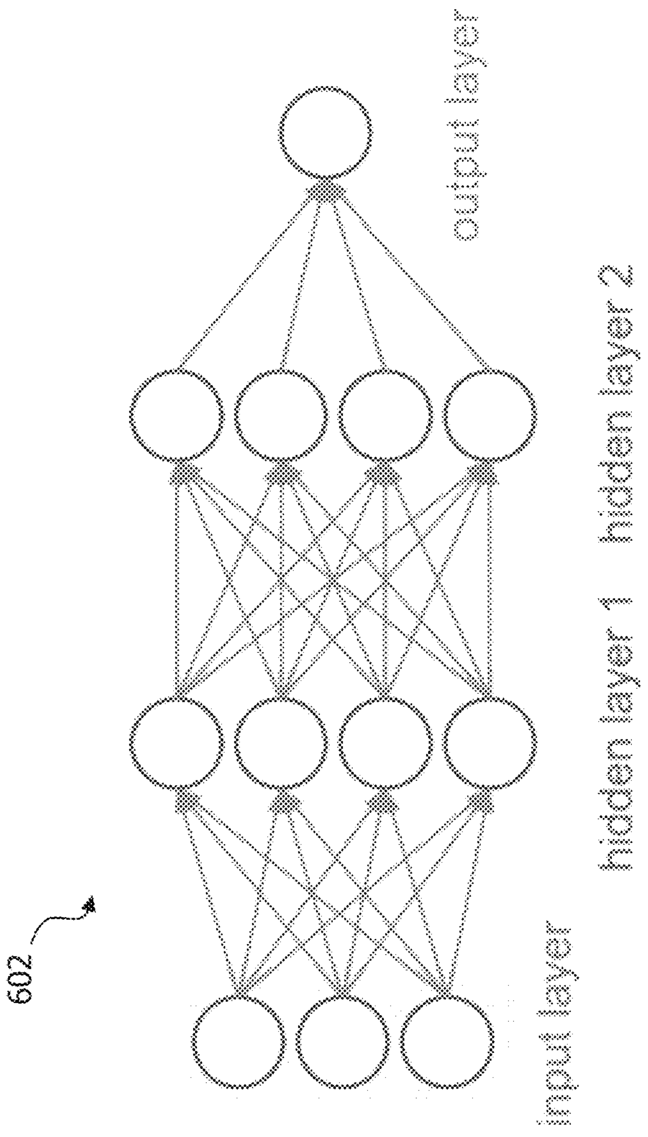
FIGS. 6*a* and 6*b* illustrate exemplary structures of the neural network according to the present disclosure.

FIG. 6*a* illustrates an exemplary structure of a neural network 602 in accordance with the present disclosure. The neural network 602 comprises an input layer, an output layer and two hidden layers. It will be understood that the neural network 602 shown in FIG. 6*a* merely illustrates the structure of deep neural networks in general and that the actual number of nodes (at least in the input layer and the hidden layers) of the neural network 602 stored in the server 404 may be significantly higher than shown in the figure. As mentioned above, a test has been performed using the 30 most influential questions among a total number of 370 questions or more (taken from standard IPIP, HEXACO-60 and BFI-10 questions and, optionally, supplemented by further questions regarding goals and motivations of the user), resulting in 30 input nodes in the input layer of the neural network 602. In such a case, each of the hidden layers could be configured with 50 nodes, for example. Further, as shown in the figure, the neural network 602 may comprise a single output node in the output layer. In this case, the result value at the output node of the output layer may be representative of the value of one personality dimension (out of the Big Five) on which the neural network 602 has been trained. It will be understood that such structure of the neural network 602 is merely exemplary and that other structures are generally conceivable.

A more advanced structure of the neural network 602 comprises input nodes in accordance with the number of a full set of questions available, which may be taken from standard IPIP, HEXACO-60 and BFI-10 questions including further questions regarding goals and motivations of the user as well as still further questions on other psychological characteristics and/or preferences of the user not covered by the above questions, potentially adding up to several hundreds of questions, e.g., more than 600 questions. Such neural network 602 may thus have more than 600 input nodes, each corresponding to one of the questions of the full set of available questions, and the number of nodes of the hidden layers may be selected depending on the performance of the neural network 602. For example, the neural network 602 may comprise two hidden layers with 100 nodes each. Further, in the input layer, the above-mentioned more than 600 input nodes may be duplicated, wherein each duplicated input node may be used as a missing-question-indicator. The missing-question-indicators may be dichotomous, i.e., they may only have two values (e.g., 0 and 1) indicating whether the question of the corresponding (original) input node has been answered or not. Due to the duplicated input nodes, the input layer may comprise a total of more than 1200 input nodes.

Figure 6B:
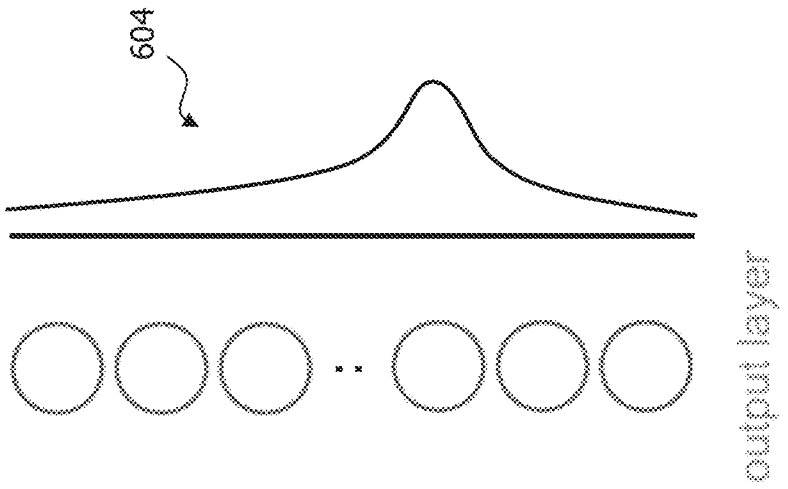

The output layer of the more advanced neural network 602 may have a plurality of output nodes that together represent a probability curve for one personality dimension. If the scale used for the output in this personality dimension ranges from 0 to 10 and the number of output nodes is 50, for example, then each output node may be representative for a portion of the scale, i.e., corresponding to the portions 0-0.2, 0.2-0.4, 0.4-0.6, . . . 9.8.10 of the scale. Instead of a single output value, such output layer may deliver a whole probability curve for the output value on this personality dimension. FIG. 6*b* illustrates an exemplary output layer together with a corresponding probability curve 604. Such curve may allow determining where the output value most probably is (i.e., indicated by the peak of the curve) as well as determining the accuracy with which the neural network 602 calculates the result (i.e., indicated by the width of the curve). Using the advanced neural network 602, it may be possible to calculate the personality data of the user in the form of several probability curves (e.g., five probability curves corresponding to the Big Five) for an arbitrary number of answered questions, provided that the neural network 602 is trained separately for each dimension. In the initial state, in which no question has been answered yet, all missing-question-indicators may have the value of "missing" (e.g., 0). With every question which is then answered, an update of the output values may be calculated so that the width of the probability curves on the output layer becomes less with an increasing number of answered questions, so that the accuracy with which the neural network 602 calculates the result steadily increases.

Such structure of the neural network 602 may be particularly advantageous because it may allow iteratively selecting questions to be answered by the user next from the full set of questions, wherein, in each iteration, a next question may be selected depending on an answer of the user to the previous question, wherein, in each iteration, a next question may be selected as a question of the full set of questions which is determined to be most influential on an achievable result for computing personality data of the user. To this end, upon each answered question, the several (e.g., five) probability curves may be recalculated and, among the recalculated probability curves, the one which has the largest width (i.e., representing the probability curve currently having the at least accuracy) may be determined. As next question for the iteration, a question on this dimension may be selected to improve the accuracy on this dimension. In order to determine the most influential question, a degree according to which a change in the digital score input to the respective input node changes the probability curve (e.g., a degree in which the width of the curve changes) may be determined for each input node of the neural network 602. Based on this, the question associated with the input node for which the degree of change in the probability curve is determined to be highest may be selected as the most influential question for the respective iteration.

The advanced structure of the neural network 602 may also be advantageous because it may allow integrating feedback easily into the neural network. As described above, if the feedback represents a new input value which has not yet been input to the neural network 602, a new input node may simply be added to the neural network 602 and the new input value may be assigned to the new input node when training the neural network 602. In this way, any kind of new feedback may easily integrated into the network so that the neural network 602 may be refine its capability to compute personality data. As an implementation which reduces the computational complexity when adding a new input node, it may be conceivable that, when the network is trained to correlate the new input node with the other nodes of the network, only those nodes may be incorporated into the calculation which are determined to be most influential with respect to the optimally achievable result, to thereby avoid incorporating all nodes into the calculation. Also, it may be conceivable that, when the network is trained to correlate the new input node with the other nodes of the network, the number of layers being precalculated is limited (e.g., to 2 or 3) to avoid calculating all subsequent combinations of nodes, for example.

In the above description, the presented technique for efficient retrieval for a digital representation of personality data of a user has been exemplified in the context of adapting a vehicle's driving configuration, such as adapting the gas and brake reaction behavior of the vehicle to the personality of the user. In this case, the method described herein may also be denoted as a method for adapting a vehicle's driving configuration including an efficient retrieval of a digital representation of personality data of a user. It will be understood that adapting the gas and brake reaction behavior of the vehicle is just one example of adapting a vehicle's driving configuration and that, more generally, adapting the vehicle's driving configuration may comprise adapting any vehicle configuration that influences the driving behavior of the vehicle. Adapting the vehicle's driving configuration may as such comprise at least one of adapting a gas and brake reaction behavior of the vehicle, adapting chassis settings of the vehicle, adapting a driving mode of the vehicle, and adapting settings of an adaptive cruise control (ACC) of the vehicle, or the like, to the personality of the user. Adapting a driving mode of the vehicle may comprise setting an economy, comfort or sport mode to influence gas pedal and fuel consumption behavior of the vehicle depending on the driver's personality. If the personality data indicates that the driver tends to be risk-averse, for example, the driving mode may be set to economy or comfort, whereas for drivers that tend to have a risk-seeking personality, the driving mode may be set to sport mode. Adapting a drive mode of the vehicle may also comprise enabling/disabling an automatic four-wheel-drive (4WD) mode of the vehicle, for example. Adapting the settings of the ACC may comprise setting the distance to the vehicle ahead and/or the target driving speed, e.g., depending on the risk-averseness of the driver.

It will be understood that the technique presented herein may also be employed for other purposes in a vehicle context, such as to adapt the environmental conditions in the passenger cabin of the vehicle (or, more generally, of a transport means, as an adaptation of the environmental conditions in the passenger cabin may similarly apply to other means of transport, such as aircrafts, trains, etc.). In this case, the method described herein may also be denoted as a method for adapting an environmental condition in a passenger cabin of a transport means including an efficient retrieval of a digital representation of personality data of a user. Adapting an environmental condition in a passenger cabin of a transport means may comprise adapting at least one of adapting a temperature of the passenger cabin (e.g., by adapting the air condition settings for the passenger cabin), adapting an internal lighting of the passenger cabin, and adapting an oxygen level in the passenger cabin, or the like, to the personality of the user. Additionally or alternatively to adapting an environmental condition in the passenger cabin, the technique presented herein may also be employed to adapt user-specific settings regarding the passenger cabin. Adapting a user-specific setting regarding a passenger cabin of a transport means may comprise adapting at least one of adapting a seat configuration (e.g., seat height, seat position, seat massage settings, seat belt tensioning, etc.) for the user in the passenger cabin, and adapting equalizer settings of a sound system (e.g., increasing/decreasing basses or heights) provided to the user in the passenger cabin, or the like, to the personality of the user.

Any of the above adaptations of vehicle/transport means settings may—in addition to the adaptation to the personality of the user—also be performed in consideration of (or "based on"/"in accordance with") sensor data indicative of a user's attention level obtained in the passenger cabin. In other words, the client device may be configured to adapt at least one of the vehicle's driving configuration, the environmental conditions in the passenger cabin, and the user-specific settings regarding the passenger cabin not only in consideration of the digital representation of the personality data of the user, but also in consideration of sensor data indicative of a user's attention level. The digital representation of the personality data of the user and the sensor data indicative of the user's attention level may in other words be combined prior to performing the above-mentioned adaptations. The sensor data indicative of the user's attention level may comprise data regarding at least one of the user's heartbeat, breath, tiredness, reaction time, and alcohol/drug level, for example. The sensor data may be collected by at least one sensor installed in the passenger cabin or in the mobile terminal of the user, for example.

Figure 7:
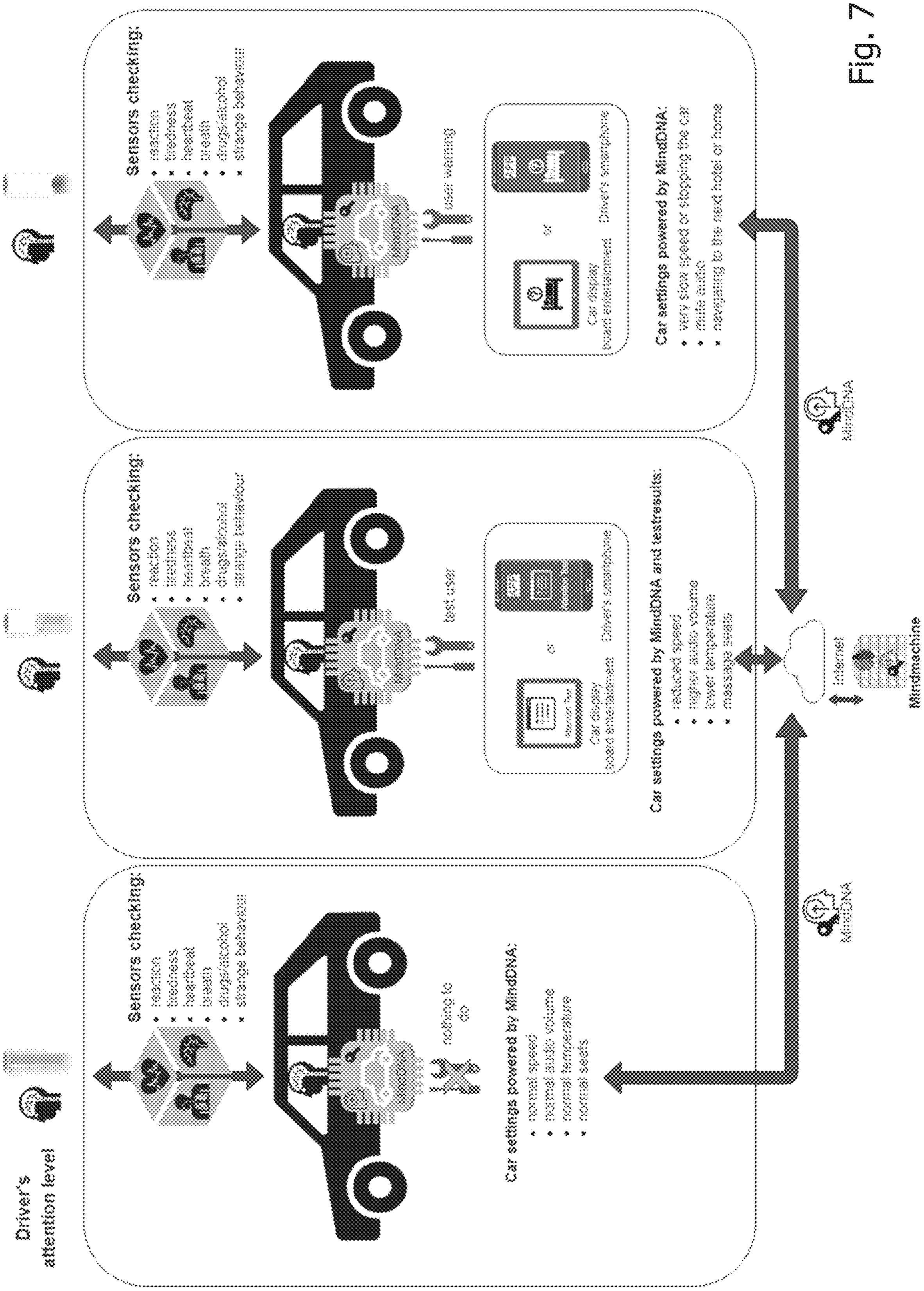
FIG. 7 illustrates an exemplary implementation which involves considering the driver's attention level to adapt settings of a vehicle according to the present disclosure.

FIG. 7 illustrates an exemplary implementation which involves considering the driver's attention level in combination with the driver's personality data in order to adapt the vehicle's driving configuration, the environmental conditions in the passenger cabin and/or the user-specific settings regarding the passenger cabin. The driver's attention level may be checked by corresponding sensors in terms of the user's reaction time, tiredness, heartbeat, breath, alcohol/drug level, or unusual behavior of the user, for example. In the left portion of the figure, the collected sensor data is indicative of a normal attention level of the user and, hence, the vehicle settings may remain at the normal levels (e.g., as adapted to the driver's personality or "MindDNA"), including the speed, audio volume, temperature and seat settings, for example. In the middle portion of the figure, the sensor data is indicative of a reduced attention level of the driver and the vehicle settings may thus be changed to reduced speed, higher audio volume, lower temperature settings, including turning on seat massage features, in order to refresh the driver's attention again. Optionally, attention tests may be performed, such as requesting the driver to provide a voice-based response in a question/answer scheme, for example, and the results of the attention tests may be considered in adapting the above-mentioned settings. In the right portion of the figure, on the other hand, the sensor data is indicative of a very low driver's attention level and, therefore, a user warning may be provided and the vehicle settings may be adapted accordingly, e.g., to a very slow speed (and forcing to stop the vehicle at the next stopping opportunity, for example), to muted audio and/or to provide directions to the next hotel by a navigation system, for example.

Figure 8:
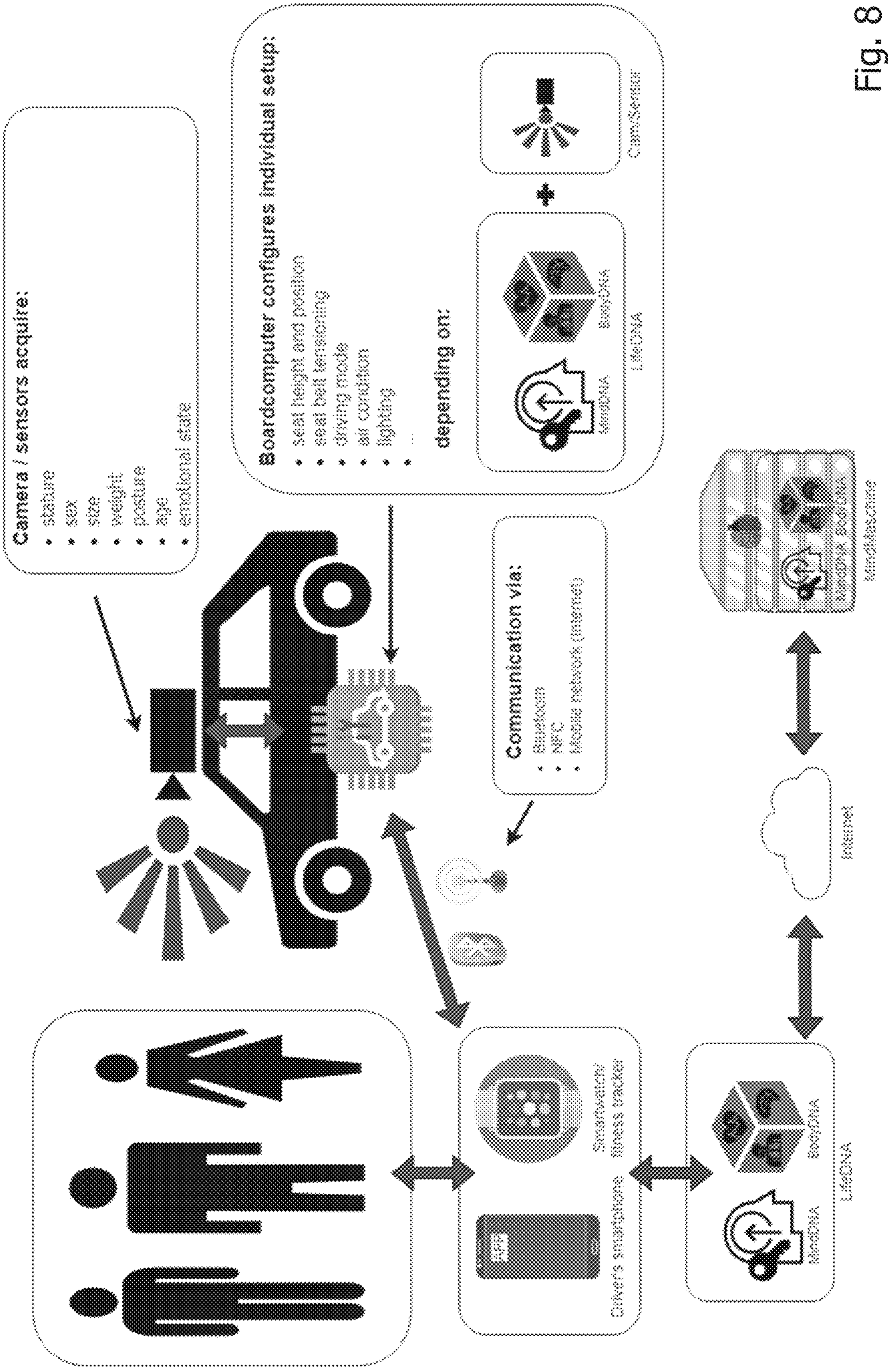
FIG. 8 illustrates an exemplary implementation which involves considering body scan data of a user to provide a user-adapted service to the user according to the present disclosure.

In order to provide a user-adapted service to the user, as described above (e.g., by adapting at least one of the vehicle's driving configuration, the environmental conditions in the passenger cabin, and the user-specific settings regarding the passenger cabin), the client device may further consider body scan data indicative of (e.g., physical) characteristics of the user derivable by scanning (e.g., at least a portion of) the user's body prior to providing the user-adapted service to the user (e.g., prior to the user driving the vehicle). The user characteristics which are derivable by scanning the user's body may include at least one of the user's size, weight, sex, age, stature, posture, and emotional state, for example. The body scan data may be obtained by a camera or voice recorder (e.g., of the mobile terminal of the user, or installed at the vehicle/transport means) acquiring one or more images or speech signals of the user, wherein body/face/voice recognition techniques may be employed to scan the user's body and derive the user characteristics mentioned above. The client device may thus be configured to provide a user-adapted service not only in consideration of the digital representation of the personality data of the user, but also in consideration of (or "based on"/"in accordance with") the body scan data. The digital representation of the personality data of the user and the body scan data may in other words be combined prior to providing the user-adapted service to the user. FIG. 8 illustrates an exemplary implementation which involves considering a driver's body scan data (e.g., obtained by the driver's mobile terminal, such as the driver's smartphone, smartwatch or fitness tracker, prior to entering the vehicle) in combination with the personality data of the driver in order to adapt the vehicle's driving configuration, the environmental conditions in the passenger cabin and/or the user-specific settings regarding the passenger cabin accordingly. In the figure, the body scan data is denoted as "BodyDNA", which in combination with the "MindDNA", forms the so-called "LifeDNA". It will be understood that the obtained body scan data may also be used to provide feedback characterizing the user to update the neural network, as described above.

In another vehicle-related use case, the technique presented herein may also be used to determine a vehicle configuration that is adapted to the personality of the user prior to manufacturing the vehicle, wherein the vehicle may then be manufactured based on (or "in accordance with") the determined vehicle configuration. The vehicle may be manufacturable in different configuration options (e.g., as offered by a vehicle manufacturer), such as with different motor options each having a different motor power, drive technology options (e.g., support of two-wheel-drive (2WD) or 4WD technology), chassis options, different drive mode options, support of ACC, etc., and when a new vehicle is to be manufactured for the user, the vehicle configuration may be determined to be specifically adapted to the personality of the user. For example, if the personality data indicates that the user tends to be risk-averse, the determined vehicle configuration may comprise a selection of a motor having a lower power as compared to a vehicle configuration determined for a user whose personality data indicates a risk-seeking personality. Based on the determined vehicle configuration, the vehicle may then be manufactured accordingly. As such, in line with the above description, it may also be envisaged a method for vehicle manufacturing including an efficient retrieval of a digital representation of personality data of a user by a client device from a server, the digital representation of the personality data being processed at the client device to provide a vehicle configuration adapted to the personality of the user. The method may comprise sending, from the client device to the server, a request for a digital representation of personality data for a user, receiving, by the client device from the server, the requested digital representation of the personality data of the user, the personality data of the user being computed, based on input obtained from the user, using a neural network trained to compute personality data for a user based on input obtained from the user, processing the digital representation of the personality data to determine a vehicle configuration which is adapted to the personality of the user, and manufacturing the vehicle based on the determined vehicle configuration. In the manufacturing process of the vehicle, it will be understood that the determined vehicle configuration may also affect the manufacturing of vehicle parts needed for the manufacturing of the vehicle. For example, manufacturing the vehicle may comprise manufacturing one or more vehicle parts to be used for manufacturing the vehicle, wherein the vehicle parts are manufactured (e.g., using a 3D printer) in accordance with the determined vehicle configuration.

It will be understood that the technique presented herein may not only be employed in vehicle/transport means related use cases, but also in other use cases, such as to adapt the configuration of smart home appliances or robots to the personality of a user, for example. As such, in line with the above description, it may also be envisaged a method for adapting a configuration of a smart home appliance (e.g., automatic roller shutters, air conditions, refrigerators, washing machines, televisions, set-top boxes, etc.) including an efficient retrieval of a digital representation of personality data of a user, wherein the digital representation of the personality of the user may be processed at the client device to adapt a configuration of the smart home appliance to the personality of the user (e.g., to adapt the way in which the smart home appliance carries out its primary task, such as its shutting (roller shutters), heating/cooling (air conditions), refrigerating (refrigerators), washing (washing machines) or recording/display (televisions/set-top boxes) tasks). Similarly, in line with the above description, it may be envisaged a method for adapting a configuration of a robot (e.g., a humanoid robot or domestic robot configured to carry out one or more household tasks) including an efficient retrieval of a digital representation of personality data of a user, wherein the digital representation of the personality of the user may be processed at the client device to adapt a configuration of the robot to the personality of the user (e.g., to adapt the way in which household tasks are carried out by the domestic robot).

Various other use cases are generally conceivable. Other use cases may comprise the adaptation of the configuration of virtual robots, the adaptation of the configuration of medical devices, or even the stimulation of a brain, for example. As such, in line with the above description, it may also be envisaged a method for adapting a configuration of a virtual robot (e.g., a chatbot, virtual service personnel or virtual personal assistant) including an efficient retrieval of a digital representation of personality data of a user, wherein the digital representation of the personality of the user may be processed at the client device to adapt a configuration of the virtual robot to the personality of the user (e.g., to adapt the way in which the virtual robot carries out its task of supporting the user). Similarly, in line with the above description, it may be envisaged a method for adapting a configuration of a medical device (e.g., a bedside medical device) including an efficient retrieval of a digital representation of personality data of a user, wherein the digital representation of the personality of the user may be processed at the client device to adapt a configuration of the medical device to the personality of the user (e.g., to adapt a dosage regime, such as the dosage of an analgesic, or the like). Even further, it may be envisaged a method for stimulating a brain (e.g., of a living being or a virtual representation of a brain) including an efficient retrieval of a digital representation of personality data of a user, wherein the digital representation of the personality of the user may be processed at the client device to adapt a stimulation procedure for the brain based on the personality of the user. The stimulation procedure may comprise an electrical stimulation of a living being's brain or an adaptation/reconfiguration of a virtual representation of a brain, for example. A virtual representation of a brain may be fed into a robot or other form of intelligent system in order to influence the behavior of such system based on the personality of the user, for example.

In all of the above-described examples and use cases, when it is referred to "adapting" a configuration or setting "to the personality of a user", it will be understood that such adaptation may be implemented using predefined mappings that map a given characteristic of the user's personality (as indicated by the digital representation of the personality data of the user) to a particular configuration or setting of the corresponding device/apparatus (e.g., vehicle, transport means, smart home appliance, robot, medical device, etc., as described above). As said, for example, if the personality data indicates that a driver tends to be risk-averse, the driving mode of a vehicle may be set to economy or comfort, whereas for drivers that tend to have a risk-seeking personality, the driving mode may be set to sport mode. Such mappings may be predefined for each possible personality characteristic-configuration/setting combination and, depending on the obtained personality data of the user, the configuration or setting of the device/apparatus may be adapted accordingly. The personality characteristic of the user may correspond to a value of a personality dimension (e.g., out of the Big Five) output by the neural network, as described above, for example.

The following numbered statements describe some various embodiments of the present invention.

Statement #1: A method may be provided for enabling efficient retrieval of a digital representation of personality data of a user (402) by a client device (502; 406) from a server (404), the digital representation of the personality data being processed at the client device (406) to provide a user-adapted service to the user (402), the method being performed by the server (404) and comprising:

storing (S202) a neural network (602) being trained to compute personality data of a user (402) based on input obtained from the user (402);

receiving (S204), from the client device (502; 406), a request for a digital representation of personality data for a user (402); and sending (S206), to the client device (502; 406), the requested digital representation of the personality data of the user (402), wherein the personality data of the user (402) is computed using the neural network (602) based on input obtained from the user (402).

Statement #2: The method according to Statement #1 may be provided, wherein the digital representation of the personality data of the user (402) is processed at the client device (502; 406) to configure at least one device (406) providing a service to the user (402), and, optionally:

wherein the at least one device (406) comprises the client device (406).

Statement #3: The method according to Statement #1 or Statement #2 may be provided, further comprising:

receiving feedback characterizing the user (402);

updating the neural network (602) based on the feedback; and sending, to the client device (502; 406), a digital representation of updated personality data of the user (402), wherein the updated personality data of the user (402) is computed using the updated neural network (602), and, optionally:

wherein the digital representation of the updated personality data of the user (402) is processed at the client device (502; 406) to refine a configuration of the at least one device (406) providing the service to the user (402).

Statement #4: The method according to Statement #3 may be provided, wherein the feedback includes behavioral data reflecting behavior of the user (402) monitored at the at least one device (406) when using the service provided by the at least one device (406), and, optionally:

wherein the behavioral data is monitored using measurements performed by the at least one device (406) providing the service to the user (402).

Statement #5: The method according to Statement #4 may be provided, wherein the at least one device (406) comprises a vehicle and wherein the behavioral data comprises data reflecting a driving behavior of the user (402).

Statement #6: The method according to any one of Statements #1 to #5 may be provided, wherein the personality data of the user (402) is computed prior to receiving the request from the client device (502; 406) and wherein the request includes an access code previously provided by the server (404) to the user (402) upon computing the personality data of the user (402), the access code allowing the user (402) to access the digital representation of the personality data of the user (402) from different client devices (502; 406).

Statement #7: The method according to any one of Statements #1 to #6 may be provided, wherein the input obtained from the user corresponds to digital scores reflecting answers to questions regarding at least one of personality, goals and motivations of the user (402) and wherein each digital score is used as input to a separate input node of the neural network (602) when computing the personality data of the user (402) using the neural network (602).

Statement #8: The method according to Statement #7 may be provided, wherein the questions correspond to questions selected from a set of questions representative of an optimally achievable result of computing personality data of a user (402), wherein the selected questions correspond to questions of the set of questions which are determined to be most influential with respect to the optimally achievable result, and, optionally:

wherein the number of the selected questions is less than 10% of the number of questions included in the set of questions.

Statement #9: The method according to Statement #8 may be provided, wherein the questions are selected from the set of questions based on correlating results achievable by each single question of the set of questions with the optimally achievable result and selecting questions from the set of questions which have a highest correlation with the optimally achievable result, or wherein the questions are selected iteratively from the set of questions, wherein, in each iteration, a next question is selected depending on an answer of the user to a previous question, wherein, in each iteration, the next question is selected as a question of the set of questions which is determined to be most influential on an achievable result for computing personality data of the user, and, optionally:

wherein the neural network (602) comprises a plurality of output nodes representative of a probability curve (604) of a result of the personality data of the user (402), wherein determining the most influential question of the set of questions as the next question of the respective iteration includes determining, for each input node of the neural network (602), a degree according to which a change in the digital score input to the respective input node of the neural network (602) changes the probability curve (604).

Statement #10: A method may be provided for enabling efficient retrieval of a digital representation of personality data of a user (402) by a client device (502; 406) from a server (404), the method being performed by the client device (502; 406) and comprising:

sending (S302), to the server (404), a request for a digital representation of personality data for a user (402);

receiving (S304), from the server (404), the requested digital representation of the personality data of the user (402), the personality data of the user (402) being computed, based on input obtained from the user (402), using a neural network (602) trained to compute personality data for a user (402) based on input obtained from the user (402); and processing (S306) the digital representation of the personality data to provide a user-adapted service to the user (402).

Statement #11: A computer program product may be provided comprising program code portions for performing the method according to any one of Statements #1 to #10 when the computer program product is executed on one or more computing units.

Statement #12: The computer program product of Statement #11 may be provided, stored on one or more computer readable recording media.

Statement #13: A server (100; 404) may be provided for enabling efficient retrieval of a digital representation of personality data of a user (402) by a client device (502; 406) from the server (404), the digital representation of the personality data being processed at the client device (502; 406) to provide a user-adapted service to the user (402), the server (404) comprising at least one processor (102) and at least one memory (104), the at least one memory (104) containing instructions executable by the at least one processor (102) such that the server (404) is operable to perform the method according to any one of Statements #1 to #9.

Statement #14: A client device (110; 502; 406) may be provided for enabling efficient retrieval of a digital representation of personality data of a user (402) from a server (404), the client device (110; 502; 406) comprising at least one processor (112) and at least one memory (114), the at least one memory (114) containing instructions executable by the at least one processor (112) such that the client device (110; 502; 406) is operable to perform the method according to Statement #10.

Statement #15: A system may be provided comprising a server (100; 404) according to Statement #13 and at least one client device (110; 502; 406) according to Statement #14.

It is believed that the advantages of the technique presented herein will be fully understood from the foregoing description, and it will be apparent that various changes may be made in the form, constructions and arrangement of the exemplary aspects thereof without departing from the scope of the disclosure or without sacrificing all of its advantageous effects. Because the technique presented herein can be varied in many ways, it will be recognized that the disclosure should be limited only by the scope of the claims that follow.

The invention claimed is:

1. A method including a retrieval of a digital representation of personality data of a user by a client device from a server, the digital representation of the personality data being processed at the client device to provide a vehicle configuration adapted to a personality the user, the method being performed by the server and comprising:

storing a neural network trained to compute user personality data based on user input;

receiving, from the client device, a request for a digital representation of personality data for the user; and sending, to the client device, the requested digital representation of the personality data of the user, wherein the personality data of the user is computed using the neural network based on input obtained from the user, wherein the digital representation of the personality data of the user is processed, prior to manufacturing a vehicle, at the client device to determine a vehicle configuration of the vehicle to be manufactured, wherein the vehicle is manufacturable in different configuration options, wherein the determined vehicle configuration is adapted to the personality of the user, and wherein the method further comprises:

receiving feedback characterizing the user;

updating the neural network based on the feedback; and sending, to the client device, a digital representation of updated personality data of the user, wherein the updated personality data of the user is computed using the updated neural network.

2. The method of claim 1, wherein the feedback is indicative of the personality of the user.

3. The method of claim 1, wherein the feedback is gathered at the client device.

4. The method of claim 1, wherein the personality data of the user is indicative of at least one of:

psychological characteristics of the user, and preferences of the user.

5. The method of claim 1, wherein the input obtained from the user corresponds to at least one answer regarding at least one of personality, goals and motivations of the user, the at least one answer given in response to at least one question posed to the user.

6. The method of claim 5, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

7. The method of claim 5, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

8. The method of claim 7, wherein the at least one question is selected from the set of questions based on correlating results achievable by each single question of the set of questions with the optimally achievable result and selecting at least one question from the set of questions having a highest correlation with the optimally achievable result.

9. The method of claim 1, wherein:

the personality data of the user is computed prior to receiving the request from the client device, and wherein the request includes an access code previously provided by the server to the user upon computing the personality data of the user, the access code allowing the user to access the digital representation of the personality data of the user from different client devices.

10. The method of claim 5, wherein:

the input obtained from the user corresponds to one or more digital scores, each digital score reflecting one of the at least one answer, and wherein each digital score is used as input to a separate input node of the neural network when computing the personality data of the user using the neural network.

11. The method of claim 7, wherein the number of the at least one selected question is less than 10% of the number of questions included in the set of questions.

12. The method of claim 7, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

13. The method of claim 12, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

14. The method of claim 1, wherein the vehicle is manufactured based on the determined vehicle configuration.

15. The method of claim 14, wherein manufacturing the vehicle comprises manufacturing one or more vehicle parts to be used for manufacturing the vehicle, and wherein the vehicle parts are manufactured in accordance with the determined vehicle configuration.

16. The method of claim 1, wherein the digital representation of the updated personality data of the user is processed at the client device to refine the vehicle configuration.

17. A method including a retrieval of a digital representation of personality data of a user by a client device from a server, the method being performed by the client device and comprising:

sending, to the server, a request for a digital representation of personality data for the user;

receiving, from the server, the requested digital representation of the personality data of the user, the personality data of the user being computed, based on input obtained from the user, using a neural network trained to compute user personality data based on user input; and processing, prior to manufacturing a vehicle, the digital representation of the personality data to determine a vehicle configuration of the vehicle to be manufactured, wherein the vehicle is manufacturable in different configuration options, wherein the determined vehicle configuration is adapted to a personality of the user, and wherein the method further comprises:

sending, to the server, feedback characterizing the user; and receiving, from the server, a digital representation of updated personality data of the user, wherein the updated personality data of the user is computed using the neural network being updated based on the feedback.

18. The method of claim 17, wherein the feedback is indicative of the personality of the user.

19. The method of claim 17, wherein the feedback is gathered at the client device.

20. The method of claim 17, wherein the personality data of the user is indicative of at least one of:

psychological characteristics of the user, and preferences of the user.

21. The method of claim 17, wherein the input obtained from the user corresponds to at least one answer regarding at least one of personality, goals and motivations of the user, the at least one answer given in response to at least one question posed to the user.

22. The method of claim 21, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

23. The method of claim 21, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

24. The method of claim 23, wherein the at least one question is selected from the set of questions based on correlating results achievable by each single question of the set of questions with the optimally achievable result and selecting at least one question from the set of questions having a highest correlation with the optimally achievable result.

25. The method of claim 17, wherein the personality data of the user is computed prior to sending the request to the server, and wherein the request includes an access code previously provided by the server to the user upon computing the personality data of the user, the access code allowing the user to access the digital representation of the personality data of the user from different client devices.

26. The method of claim 21, wherein the input obtained from the user corresponds to one or more digital scores, each digital score reflecting one of the at least one answer, and wherein each digital score is used as input to a separate input node of the neural network when computing the personality data of the user using the neural network.

27. The method of claim 23, wherein the number of the at least one selected question is less than 10% of the number of questions included in the set of questions.

28. The method of claim 23, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

29. The method of claim 28, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

30. The method of claim 17, wherein the vehicle is manufactured based on the determined vehicle configuration.

31. The method of claim 30, wherein manufacturing the vehicle comprises manufacturing one or more vehicle parts to be used for manufacturing the vehicle, and wherein the vehicle parts are manufactured in accordance with the determined vehicle configuration.

32. The method of claim 17, wherein the digital representation of the updated personality data of the user is processed at the client device to refine the vehicle configuration.

33. A method including a retrieval of a digital representation of personality data of a user, the digital representation of the personality data being processed to provide a vehicle configuration adapted to a personality of the user, the method comprising:

obtaining a digital representation of personality data of the user, the personality data of the user being computed, based on input obtained from the user, using a neural network trained to compute user personality data based on user input; and processing, prior to manufacturing a vehicle, the digital representation of the personality data to determine a vehicle configuration of the vehicle to be manufactured, wherein the vehicle is manufacturable in different configuration options, wherein the determined vehicle configuration is adapted to the personality of the user, and wherein the method further comprises:

obtaining feedback characterizing the user; and obtaining a digital representation of updated personality data of the user, wherein the updated personality data of the user is computed using the neural network in a state in which updating the neural network has been performed based on the feedback.

34. The method of claim 33, wherein the feedback is indicative of the personality of the user.

35. The method of claim 33, wherein the feedback is gathered at a client device.

36. The method of claim 33, wherein the personality data of the user is indicative of at least one of:

psychological characteristics of the user, and preferences of the user.

37. The method of claim 33, wherein the input obtained from the user corresponds to at least one answer regarding at least one of personality, goals and motivations of the user, the at least one answer given in response to at least one question posed to the user.

38. The method of claim 37, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

39. The method of claim 37, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

40. The method of claim 39, wherein the at least one question is selected from the set of questions based on correlating results achievable by each single question of the set of questions with the optimally achievable result and selecting at least one question from the set of questions having a highest correlation with the optimally achievable result.

41. The method of claim 33, wherein the personality data of the user is computed prior to receiving a request for the digital representation of the personality data of the user, and wherein the request includes an access code previously provided to the user upon computing the personality data of the user, the access code allowing the user to access the digital representation of the personality data of the user from different client devices.

42. The method of claim 37, wherein the input obtained from the user corresponds to one or more digital scores, each digital score reflecting one of the at least one answer, and wherein each digital score is used as input to a separate input node of the neural network when computing the personality data of the user using the neural network.

43. The method of claim 39, wherein the number of the at least one selected question is less than 10% of the number of questions included in the set of questions.

44. The method of claim 39, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

45. The method of claim 44, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

46. The method of claim 33, wherein the vehicle is manufactured based on the determined vehicle configuration.

47. The method of claim 46, wherein manufacturing the vehicle comprises manufacturing one or more vehicle parts to be used for manufacturing the vehicle, and wherein the vehicle parts are manufactured in accordance with the determined vehicle configuration.

48. The method of claim 33, wherein the digital representation of the updated personality data of the user is processed to refine the vehicle configuration.

49. One or more non-transitory computer readable recording mediums storing a computer program product executable by a server for at least a retrieval of a digital representation of personality data of a user by a client device from the server, the digital representation of the personality data being processed at the client device to provide a vehicle configuration adapted to a personality of the user, the computer program product comprising:

storage instructions configured to cause storage of a neural network trained to compute user personality data based on user input;

first receiving instructions configured to cause receiving, from the client device, of a request for a digital representation of personality data for the user; and first sending instructions configured to cause sending, to the client device, of the requested digital representation of the personality data of the user, wherein the personality data of the user is computed using the neural network based on input obtained from the user, wherein the digital representation of the personality data of the user is processed, prior to manufacturing a vehicle, at the client device to determine a vehicle configuration of the vehicle to be manufactured, wherein the vehicle is manufacturable in different configuration options, wherein the determined vehicle configuration is adapted to the personality of the user, and wherein the computer program product further comprises:

second receiving instructions configured to cause receiving of feedback characterizing the user;

updating instructions configured to cause updating of the neural network based on the feedback; and second sending instructions configured to cause sending, to the client device, of a digital representation of updated personality data of the user, wherein the updated personality data of the user is computed using the updated neural network.

50. One or more non-transitory computer readable recording mediums storing a computer program product executable by a client device for at least a retrieval of a digital representation of personality data of a user by the client device from a server, the computer program product comprising:

first sending instructions configured to cause sending, to the server, of a request for a digital representation of personality data for the user;

first receiving instructions configured to cause receiving, from the server, of the requested digital representation of the personality data of the user, the personality data of the user being computed, based on input obtained from the user, using a neural network trained to compute user personality data based on user input; and processing instructions configured to cause processing, prior to manufacturing a vehicle, of the digital representation of the personality data to determine a vehicle configuration of the vehicle to be manufactured, wherein the vehicle is manufacturable in different configuration options, wherein the determined vehicle configuration is adapted to a personality of the user, and wherein the computer program product further comprises:

second sending instructions configured to cause sending, to the server, of feedback characterizing the user; and second receiving instructions configured to cause receiving, from the server, of a digital representation of updated personality data of the user, wherein the updated personality data of the user is computed using the neural network being updated based on the feedback.

51. One or more non-transitory computer readable recording mediums storing a computer program product executable by at least one processor for at least a retrieval of a digital representation of personality data of a user, the digital representation of the personality data being processed to provide a vehicle configuration adapted to a personality of the user, the computer program product comprising:

obtaining instructions configured to cause obtaining of a digital representation of personality data of the user, the personality data of the user being computed, based on input obtained from the user, using a neural network trained to compute user personality data based on user input; and processing instructions configured to cause processing, prior to manufacturing a vehicle, of the digital representation of the personality data to determine a vehicle configuration of the vehicle to be manufactured, wherein the vehicle is manufacturable in different configuration options, wherein the determined vehicle configuration is adapted to the personality of the user, and wherein the computer program product further comprises:

first obtaining instructions configured to cause obtaining of feedback characterizing the user; and second obtaining instructions configured to cause obtaining of a digital representation of updated personality data of the user, wherein the updated personality data of the user is computed using the neural network in a state in which updating the neural network has been performed based on the feedback.

52. A server comprising at least one processor and at least one memory, the at least one memory containing instructions executable by the at least one processor at least for a retrieval of a digital representation of personality data of a user by a client device from the server, the digital representation of the personality data being processed at the client device to provide a vehicle configuration adapted to a personality of the user, and the at least one memory containing the instructions executable by the at least one processor such that the server is operable at least to:

store a neural network trained to compute user personality data based on user input;

receive, from the client device, a request for a digital representation of personality data for the user; and send, to the client device, the requested digital representation of the personality data of the user, wherein the personality data of the user is computed using the neural network based on input obtained from the user, wherein the digital representation of the personality data of the user is processed, prior to manufacturing a vehicle, at the client device to determine a vehicle configuration of the vehicle to be manufactured, wherein the vehicle is manufacturable in different configuration options, wherein the determined vehicle configuration is adapted to the personality of the user, and wherein the at least one memory contains the instructions executable by the at least one processor such that the server is further operable at least to:

receive feedback characterizing the user;

update the neural network based on the feedback; and send, to the client device, a digital representation of updated personality data of the user, wherein the updated personality data of the user is computed using the updated neural network.

53. A client device comprising at least one processor and at least one memory, the at least one memory containing instructions executable by the at least one processor at least for a retrieval of a digital representation of personality data of a user by the client device from a server, and the at least one memory containing the instructions executable by the at least one processor such that the client device is operable at least to:

send, to the server, a request for a digital representation of personality data for the user;

receive, from the server, the requested digital representation of the personality data of the user, the personality data of the user being computed, based on input obtained from the user, using a neural network trained to compute user personality data based on user input; and process, prior to manufacturing a vehicle, the digital representation of the personality data to determine a vehicle configuration of the vehicle to be manufactured, wherein the vehicle is manufacturable in different configuration options, wherein the determined vehicle configuration is adapted to a personality of the user, and wherein the at least one memory contains the instructions executable by the at least one processor such that the client device is further operable at least to:

send, to the server, feedback characterizing the user; and receive, from the server, a digital representation of updated personality data of the user, wherein the updated personality data of the user is computed using the neural network being updated based on the feedback.

54. The one or more non-transitory computer readable recording mediums of claim 49, wherein the feedback is indicative of the personality of the user.

55. The one or more non-transitory computer readable recording mediums of claim 49, wherein the feedback is gathered at the client device.

56. The one or more non-transitory computer readable recording mediums of claim 49, wherein the personality data of the user is indicative of at least one of:

psychological characteristics of the user, and preferences of the user.

57. The one or more non-transitory computer readable recording mediums of claim 49, wherein the input obtained from the user corresponds to at least one answer regarding at least one of personality, goals and motivations of the user, the at least one answer given in response to at least one question posed to the user.

58. The one or more non-transitory computer readable recording mediums of claim 57, wherein the at least one answer regarding the personality of the user corresponds to at least one answer to at least one question of at least one of:

an International Personality Item Pool, IPIP,
a HEXACO-60 pool,
a Big-Five-Inventory-10, BFI-10, pool,
questions on psychological characteristics of the user, and
questions on preferences of the user.

59. The one or more non-transitory computer readable recording mediums of claim 57, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

60. The one or more non-transitory computer readable recording mediums of claim 59, wherein the at least one question is selected from the set of questions based on correlating results achievable by each single question of the set of questions with the optimally achievable result and selecting at least one question from the set of questions having a highest correlation with the optimally achievable result.

61. The one or more non-transitory computer readable recording mediums of claim 59, wherein the personality data of the user is computed prior to receiving the request from the client device, and wherein the request includes an access code previously provided by the server to the user upon computing the personality data of the user, the access code allowing the user to access the digital representation of the personality data of the user from different client devices.

62. The one or more non-transitory computer readable recording mediums of claim 57, wherein the input obtained from the user corresponds to one or more digital scores, each digital score reflecting one of the at least one answer, and wherein each digital score is used as input to a separate input node of the neural network when computing the personality data of the user using the neural network.

63. The one or more non-transitory computer readable recording mediums of claim 59, wherein the number of the at least one selected question is less than 10% of the number of questions included in the set of questions.

64. The one or more non-transitory computer readable recording mediums of claim 59, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

65. The one or more non-transitory computer readable recording mediums of claim 64, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

66. The one or more non-transitory computer readable recording mediums of claim 49, wherein the vehicle is manufactured based on the determined vehicle configuration.

67. The one or more non-transitory computer readable recording mediums of claim 66, wherein manufacturing the vehicle comprises manufacturing one or more vehicle parts to be used for manufacturing the vehicle, and wherein the vehicle parts are manufactured in accordance with the determined vehicle configuration.

68. The one or more non-transitory computer readable recording mediums of claim 49, wherein the digital representation of the updated personality data of the user is processed at the client device to refine the vehicle configuration.

69. The one or more non-transitory computer readable recording mediums of claim 50, wherein the feedback is indicative of the personality of the user.

70. The one or more non-transitory computer readable recording mediums of claim 50, wherein the feedback is gathered at the client device.

71. The one or more non-transitory computer readable recording mediums of claim 50, wherein the personality data of the user is indicative of at least one of:

psychological characteristics of the user, and
preferences of the user.

72. The one or more non-transitory computer readable recording mediums of claim 50, wherein the input obtained from the user corresponds to at least one answer regarding at least one of personality, goals and motivations of the user, the at least one answer given in response to at least one question posed to the user.

73. The one or more non-transitory computer readable recording mediums of claim 72, wherein the at least one answer regarding the personality of the user corresponds to at least one answer to at least one question of at least one of:

an International Personality Item Pool, IPIP,
a HEXACO-60 pool,
a Big-Five-Inventory-10, BFI-10, pool,
questions on psychological characteristics of the user, and
questions on preferences of the user.

74. The one or more non-transitory computer readable recording mediums of claim 72, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

75. The one or more non-transitory computer readable recording mediums of claim 74, wherein the at least one question is selected from the set of questions based on correlating results achievable by each single question of the set of questions with the optimally achievable result and selecting at least one question from the set of questions having a highest correlation with the optimally achievable result.

76. The one or more non-transitory computer readable recording mediums of claim 50, wherein the personality data of the user is computed prior to sending the request to the server, and wherein the request includes an access code previously provided by the server to the user upon computing the personality data of the user, the access code allowing the user to access the digital representation of the personality data of the user from different client devices.

77. The one or more non-transitory computer readable recording mediums of claim 72, wherein the input obtained from the user corresponds to one or more digital scores, each digital score reflecting one of the at least one answer, and wherein each digital score is used as input to a separate input node of the neural network when computing the personality data of the user using the neural network.

78. The one or more non-transitory computer readable recording mediums of claim 74, wherein the number of the at least one selected question is less than 10% of the number of questions included in the set of questions.

79. The one or more non-transitory computer readable recording mediums of claim 74, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

80. The one or more non-transitory computer readable recording mediums of claim 79, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

81. The one or more non-transitory computer readable recording mediums of claim 50, wherein the vehicle is manufactured based on the determined vehicle configuration.

82. The one or more non-transitory computer readable recording mediums of claim 81, wherein manufacturing the vehicle comprises manufacturing one or more vehicle parts to be used for manufacturing the vehicle, and wherein the vehicle parts are manufactured in accordance with the determined vehicle configuration.

83. The one or more non-transitory computer readable recording mediums of claim 50, wherein the digital representation of the updated personality data of the user is processed at the client device to refine the vehicle configuration.

84. The one or more non-transitory computer readable recording mediums of claim 51, wherein the feedback is indicative of the personality of the user.

85. The one or more non-transitory computer readable recording mediums of claim 51, wherein the feedback is gathered at a client device.

86. The one or more non-transitory computer readable recording mediums of claim 51, wherein the personality data of the user is indicative of at least one of:

psychological characteristics of the user, and preferences of the user.

87. The one or more non-transitory computer readable recording mediums of claim 51, wherein the input obtained from the user corresponds to at least one answer regarding at least one of personality, goals and motivations of the user, the at least one answer given in response to at least one question posed to the user.

88. The one or more non-transitory computer readable recording mediums of claim 87, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

89. The one or more non-transitory computer readable recording mediums of claim 87, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

90. The one or more non-transitory computer readable recording mediums of claim 89, wherein the at least one question is selected from the set of questions based on correlating results achievable by each single question of the set of questions with the optimally achievable result and selecting at least one question from the set of questions having a highest correlation with the optimally achievable result.

91. The one or more non-transitory computer readable recording mediums of claim 51, wherein the personality data of the user is computed prior to receiving a request for the digital representation of the personality data of the user, and wherein the request includes an access code previously provided to the user upon computing the personality data of the user, the access code allowing the user to access the digital representation of the personality data of the user from different client devices.

92. The one or more non-transitory computer readable recording mediums of claim 87, wherein the input obtained from the user corresponds to one or more digital scores, each digital score reflecting one of the at least one answer, and wherein each digital score is used as input to a separate input node of the neural network when computing the personality data of the user using the neural network.

93. The one or more non-transitory computer readable recording mediums of claim 89, wherein the number of the at least one selected question is less than 10% of the number of questions included in the set of questions.

94. The one or more non-transitory computer readable recording mediums of claim 89, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

95. The one or more non-transitory computer readable recording mediums of claim 94, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

96. The one or more non-transitory computer readable recording mediums of claim 51, wherein the vehicle is manufactured based on the determined vehicle configuration.

97. The one or more non-transitory computer readable recording mediums of claim 96, wherein manufacturing the vehicle comprises manufacturing one or more vehicle parts to be used for manufacturing the vehicle, and wherein the vehicle parts are manufactured in accordance with the determined vehicle configuration.

98. The one or more non-transitory computer readable recording mediums of claim 51, wherein the digital representation of the updated personality data of the user is processed to refine the vehicle configuration.

99. The server of claim 52, wherein the feedback is indicative of the personality of the user.

100. The server of claim 52, wherein the feedback is gathered at the client device.

101. The server of claim 52, wherein the personality data of the user is indicative of at least one of:

psychological characteristics of the user, and preferences of the user.

102. The server of claim 52, wherein the input obtained from the user corresponds to at least one answer regarding at least one of personality, goals and motivations of the user, the at least one answer given in response to at least one question posed to the user.

103. The server of claim 102, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

104. The server of claim 102, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

105. The server of claim 104, wherein the at least one question is selected from the set of questions based on correlating results achievable by each single question of the set of questions with the optimally achievable result and selecting at least one question from the set of questions having a highest correlation with the optimally achievable result.

106. The server of claim 52, wherein the personality data of the user is computed prior to receiving the request from the client device, and wherein the request includes an access code previously provided by the server to the user upon computing the personality data of the user, the access code allowing the user to access the digital representation of the personality data of the user from different client devices.

107. The server of claim 102, wherein the input obtained from the user corresponds to one or more digital scores, each digital score reflecting one of the at least one answer, and wherein each digital score is used as input to a separate input node of the neural network when computing the personality data of the user using the neural network.

108. The server of claim 104, wherein the number of the at least one selected question is less than 10% of the number of questions included in the set of questions.

109. The server of claim 104, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

110. The server of claim 109, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

111. The server of claim 52, wherein the vehicle is manufactured based on the determined vehicle configuration.

112. The server of claim 111, wherein manufacturing the vehicle comprises manufacturing one or more vehicle parts to be used for manufacturing the vehicle, and wherein the vehicle parts are manufactured in accordance with the determined vehicle configuration.

113. The server of claim 52, wherein the digital representation of the updated personality data of the user is processed at the client device to refine the vehicle configuration.

114. The client device of claim 53, wherein the feedback is indicative of the personality of the user.

115. The client device of claim 53, wherein the feedback is gathered at the client device.

116. The client device of claim 53, wherein the personality data of the user is indicative of at least one of:

psychological characteristics of the user, and preferences of the user.

117. The client device of claim 53, wherein the input obtained from the user corresponds to at least one answer regarding at least one of personality, goals and motivations of the user, the at least one answer given in response to at least one question posed to the user.

118. The client device of claim 117, wherein the at least one answer regarding the personality of the user corresponds to at least one answer to at least one question of at least one of:

an International Personality Item Pool, IPIP, a HEXACO-60 pool, a Big-Five-Inventory-10, BFI-10, pool, questions on psychological characteristics of the user, and questions on preferences of the user.

119. The client device of claim 117, wherein the at least one question corresponds to at least one question selected from a set of questions representative of an optimally achievable result of computing personality data of a user, and wherein the at least one selected question corresponds to at least one question of the set of questions determined to be most influential with respect to the optimally achievable result.

120. The client device of claim 119, wherein the at least one question is selected from the set of questions based on correlating results achievable by each single question of the set of questions with the optimally achievable result and selecting at least one question from the set of questions having a highest correlation with the optimally achievable result.

121. The client device of claim 53, wherein the personality data of the user is computed prior to sending the request to the server, and wherein the request includes an access code previously provided by the server to the user upon computing the personality data of the user, the access code allowing the user to access the digital representation of the personality data of the user from different client devices.

122. The client device of claim 117, wherein the input obtained from the user corresponds to one or more digital scores, each digital score reflecting one of the at least one answer, and wherein each digital score is used as input to a separate input node of the neural network when computing the personality data of the user using the neural network.

123. The client device of claim 119, wherein the number of the at least one selected question is less than 10% of the number of questions included in the set of questions.

124. The client device of claim 119, wherein the at least one question is selected iteratively from the set of questions, wherein, in each iteration, a next question is selected depending on an answer of the user to a previous question, and wherein, in each iteration, the next question is selected as a question of the set of questions which is determined to be most influential on an achievable result for computing personality data of the user.

125. The client device of claim 124, wherein the neural network comprises a plurality of output nodes representative of a probability curve of a result of the personality data of the user, and wherein determining the most influential question of the set of questions as the next question of the respective iteration includes determining, for each input node of the neural network, a degree according to which a change in a digital score input to the respective input node of the neural network changes the probability curve.

126. The client device of claim 53, wherein the vehicle is manufactured based on the determined vehicle configuration.

127. The client device of claim 126, wherein manufacturing the vehicle comprises manufacturing one or more vehicle parts to be used for manufacturing the vehicle, and wherein the vehicle parts are manufactured in accordance with the determined vehicle configuration.

128. The client device of claim 53, wherein the digital representation of the updated personality data of the user is processed at the client device to refine the vehicle configuration.

* * * * *